United States Patent
Aziz

(10) Patent No.: US 10,365,242 B2
(45) Date of Patent: Jul. 30, 2019

(54) ELECTROCHEMICAL CELL FOR DETECTING HYDROQUINONE

(71) Applicant: KING FAHD UNIVERSITY OF PETROLEUM AND MINERALS, Dhahran (SA)

(72) Inventor: Md. Abdul Aziz, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 127 days.

(21) Appl. No.: 15/724,747

(22) Filed: Oct. 4, 2017

(65) Prior Publication Data
US 2019/0101502 A1    Apr. 4, 2019

(51) Int. Cl.
| | |
|---|---|
| *G01N 27/30* | (2006.01) |
| *C01B 32/205* | (2017.01) |
| *G01N 27/416* | (2006.01) |
| *G01N 27/413* | (2006.01) |
| *C25B 11/12* | (2006.01) |
| *C01B 32/05* | (2017.01) |

(52) U.S. Cl.
CPC .......... *G01N 27/308* (2013.01); *C01B 32/05* (2017.08); *C01B 32/205* (2017.08); *C25B 11/12* (2013.01); *G01N 27/301* (2013.01); *G01N 27/413* (2013.01); *G01N 27/4168* (2013.01)

(58) Field of Classification Search
CPC .. C25B 11/12; G01N 27/327; G01N 27/3271; G01N 27/308; G01N 27/333
See application file for complete search history.

(56) References Cited

U.S. PATENT DOCUMENTS

| | | |
|---|---|---|
| 9,346,678 B1 | 5/2016 | Alshehri et al. |
| 2013/0089738 A1 | 4/2013 | Al-Zahrani et al. |

FOREIGN PATENT DOCUMENTS

| | | |
|---|---|---|
| CN | 102557026 A | 7/2012 |
| CN | 105836745 A | 8/2016 |

OTHER PUBLICATIONS

Ali et al., "Superior supercapacitve performance in porous nanocarbons," Journal of Energy Chemistry 25 (2016) 734-739 (Year: 2016).*
Shoaib et al., "Optimization and characterization of sliced activated carbon prepared from date palm tree fronds by physical activation," Biomass and Bioenergy 73 (2015) 124-134 (Year: 2015).*
An article on the Gamry Instruments website entitled "Two, Three and Four Electrode Experiments" ("Gamry"), downloaded from https://web.archive.org/web/20161122203033/https://www.gamry.com/application-notes/electrodes-cells/two-three-and-four-electrode-experiments/, published Nov. 22, 2016 (Year: 2016).*

(Continued)

*Primary Examiner* — Alexander S Noguerola
(74) *Attorney, Agent, or Firm* — Oblon, McClelland, Maier & Neustadt, L.L.P.

(57) ABSTRACT

An electrode that comprises a nanostructured material that comprises pyrolyzed date palm leaves that are obtained from a pyrolysis of an agro-waste containing date palm leaves in an inert gas and in a temperature range of 800 to 1600° C., an electrochemical cell thereof, and a method of determining a hydroquinone concentration in a hydroquinone-containing solution with the electrochemical cell. Various combinations of embodiments are also provided.

19 Claims, 20 Drawing Sheets

(56) References Cited

OTHER PUBLICATIONS

Singh et al., Physisorbed Hydroquinone on Activated Charcoal as a Supercapacitor: An Application of Proton-Coupled Electrode Transfer, J. Phys. Chem. C 2015, 119, 11382-11390 (Year: 2015).*

Wang et al. "A simultaneous and Sensitive Determination of Hydroquinone and Catechol at Anodically Pretreated Screen-Printed Carbon Electrodes," Int. J. Electrochem. Sci., 5 (2010) 1649-1664 (Year: 2010).*

Sim et al., "Electrochemical Performance of Activated Carbon Derived from Treated Food-Waste," Int. J. Elecrochem. Sci. 10 (2015) 10157-10172 (Year: 2015).*

Chao Peng, et al., "Promising activated carbons derived from waste tea-leaves and their application in high performance supercapacitors electrodes", Electrochimica Acta, vol. 87, Jan. 1, 2013, pp. 401-408.

Mandakini Biswal, et al., "From dead leaves to high energy density supercapacitors", Energy & Environmental Science, vol. 6, Issue 4, Feb. 2013, pp. 1249-1259.

Adekunle Moshood Abioye, et al., "Recent development in the production of activated carbon electrodes from agricultural waste biomass for supercapacitors: A review", Renewable and Sustainable Energy Reviews, vol. 52, Dec. 2015, pp. 1282-1293.

H. Hadoun, et al., "Characterization of mesoporous carbon prepared from date stems by $H_3PO_4$ chemical activation", Applied Surface Science. vol. 280, Sep. 1, 2013, pp. 1-7.

Rehab Abd Almohsen, "Oman's chemists use palm leaves for water treatment" Sci Dev Net, http://www.scidev.net/global/pollution/news/oman-s-chemists-use-palm-leaves-for-water-treatment-.html, Dec. 3, 2012, 3 pages.

Md. Azharul Islam, et al., "Mesoporous and adsorptive properties of palm date seed activated carbon prepared via sequential hydrothermal carbonization and sodium hydroxide activation", Chemical Engineering Journal, vol. 270, 2015, pp. 187-195.

Falah H. Hussein, et al., "Preparation and Characterization of Activated Carbon from Iraqi Khestawy Date Palm", Journal of Chemistry, vol. 2015, 2015, 8 pages.

Zainab Mahdi, et al., "Date Palm (*Phoenix riactylifera* L.) Seed Characterization for Blocher Preparation", The $6^{TH}$ International Conference on Engineering, Sep. 2015, pp. 130-138.

Tanweer Ahmad, et al., "The use of date palm as a potential adsorbentfor wastewater treatment: a review", Environ Sci Pollut Res, vol. 19, 2012, pp. 1464-1484.

K. Suresh Kumar Reddy, et al., "Activated Carbon from Date Palm Seed: Process Optimization Using Response Surface Methodology", Waste Biomass Valor, vol. 3, 2012, pp. 149-156.

M.N. Alaya, et al., "Activated Carbon from Some Agricultural Wastes Linder Action of One-Step Steam Pyrolysis". Journal of Porous Materials, vol. 7, 2000, pp. 509-517.

O. Houache, et al., "Study of Date Palm Stem as Raw Material in Preparation of Activated Carbon", The Journal of Engineering Research, vol. 5, No. 1, 2008, pp. 47-54.

Muhammad Shoaib, et al., "Effect of $CO_2$ Flow Rate on the Synthesis of Sliced Activated Carbon from Date Palm Tree Fronds (Agro Waste) by Physical Activation", Asian Journal of Chemistry, vol. 26, No. 20, 2014, pp. 7025-7028.

Mohammed Danish, et al., "Optimized preparation for large surface area activated carbon from date (*Phoenix dactylifera* L.) stone biomass", Biomass and Bioenergy, vol. 61, 2014, pp. 167-178.

* cited by examiner

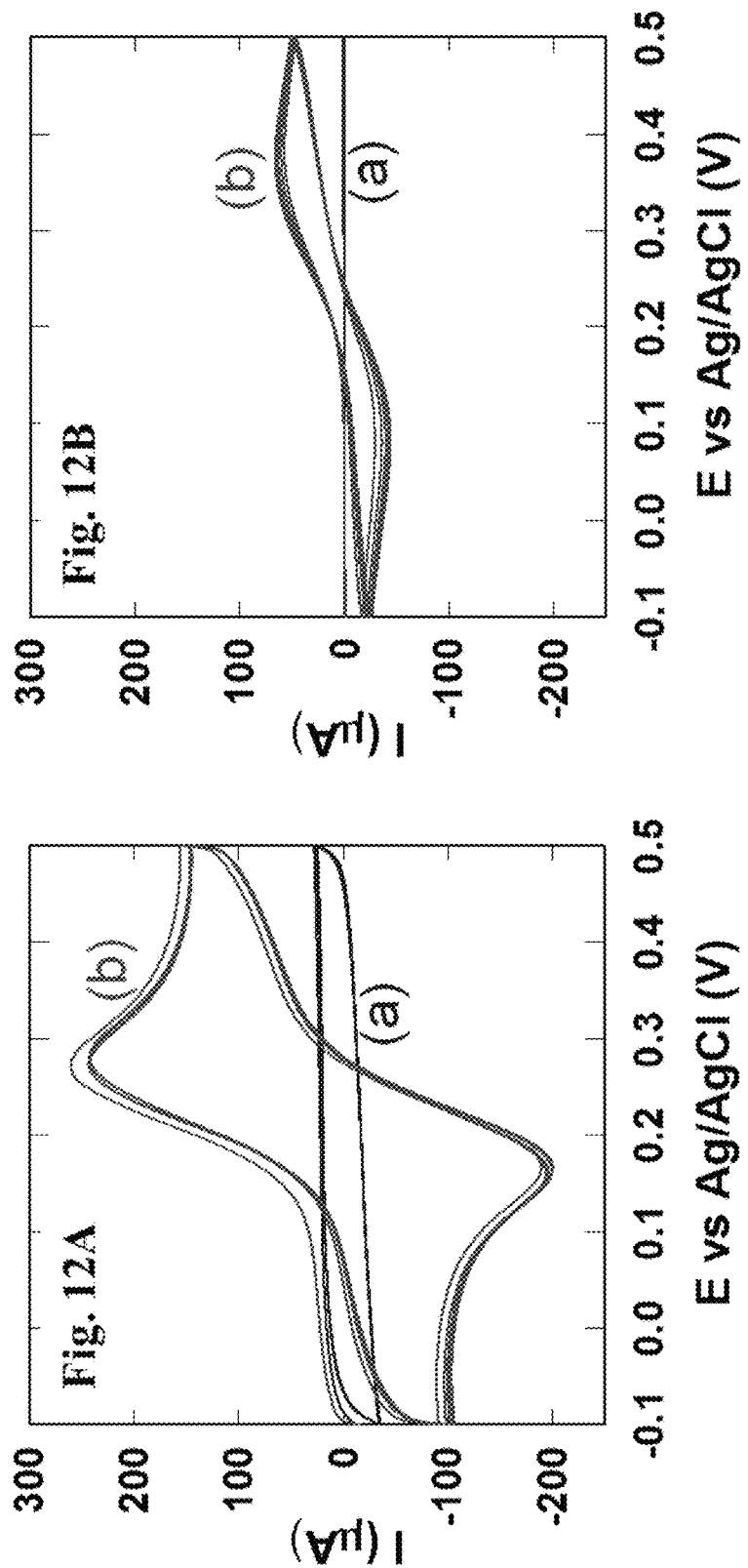

ELECTROCHEMICAL CELL FOR DETECTING HYDROQUINONE

STATEMENT OF FUNDING ACKNOWLEDGEMENT

The funding support provided by Center of Excellence in Nanotechnology (CENT) at King Fahd University of Petroleum and Minerals is gratefully acknowledged.

STATEMENT REGARDING PRIOR DISCLOSURES BY THE INVENTOR OR A JOINT INVENTOR

Aziz et al., *A simple and direct preparation of a substrate-free interconnected nanostructured carbon electrode from date palm leaflets for detecting hydroquinone*. Chemistry-Select, Volume 2, Issue 17, Jun. 12, 2017, Pages 4787-4793, which is incorporated by reference in its entirety.

BACKGROUND OF THE INVENTION

Technical Field

The present invention relates to an electrode that comprises a nanostructured material based on pyrolyzed date palm leaves that are obtained from a pyrolysis of an agro-waste, an electrochemical cell thereof, and a method of determining a hydroquinone concentration in a hydroquinone-containing solution.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Carbon materials are widely used in various applications such as adsorbing heavy metals and environmental pollutants, filtering water, manufacturing catalyst materials, manufacturing pharmaceutical, manufacturing inks and toners, etc. Therefore, producing carbon materials from inexpensive sources, particularly from biomass/agro-waste sources, is an important aspect to reduce manufacturing cost of the final products produced from carbon materials [Li H-Y, Chen H-Z, Xu W-J, Yuan F, Wang J-R, Wang M, (2005) Polymer-encapsulated hydrophilic carbon black nanoparticles free from aggregation, Colloids and Surfaces A: Physicochem. Eng. Aspects, 254: 173-178; M. S. Islam, M. A. Rouf, (2012) Waste biomass as sources for activated carbon production-A review, Bangladesh J. Sci. Ind. Res., 47: 347-364; Alkhati A J, Zailaey K A, (2015) Medical and environmental applications of activated charcoal: review article, European scientific journal, 11: 50-56; Tan J S, Ani F N, (2004) Carbon molecular sieves produced from oil palm shell for air separation, Separation and Purification Technology, 35: 47-54; Ahmad T, Danish M, Rafatullah M, Ghazali A, Sulaiman O, Hashim R, Ibrahim M N M, (2012) The use of date palm as a potential adsorbent for wastewater treatment: a review, Environ Sci. Pollut. Res 19: 1464-1484]. Carbon materials are widely used as adsorbents, catalysts, and catalyst supports [M. S. Islam, M. A. Rouf, (2012) Waste biomass as sources for activated carbon production-A review, Bangladesh J. Sci. Ind. Res., 47: 347-364; Meryemoglu B, Irmak S, Hasanoglu A, (2016) Fuel Processing Technology, 151: 59-63; Tsoncheva T, Genova I, Stoycheva I, Spassova I, Ivanova R, Tsyntsarski B, Issa G, Kovacheva D, Petrov, (2015) Activated carbon from waste biomass as catalyst support: formation of active phase in copper and cobalt catalysts for methanol decomposition, J. Porous Mater, 22: 1127-1136; Azargohar R, (2009) Production of activated carbon and its catalytic application for oxidation of hydrogen sulfide, A PhD Thesis in in the department of chemical engineering, University of Saskatchewan, Saskatoon, Saskatchewan]. In addition, carbon materials are widely used in the composition of electrodes in electrochemical sensors, capacitors, fuel cells, and solar cells, etc. [Abioye A M, Ani F N, (2015) Recent development in the production of activated carbon electrodes from agricultural waste biomass for supercapacitors: A review, Renewable and Sustainable Energy Reviews, 52: 1282-1293; Veeramani V, Madhu R, Chen S-M, Lou B-S, Palanisamy J, Vasanth V S, (2015) Biomass-derived functional porous carbons as novel electrode material for the practical detection of biomolecules in human serum and snail hemolymph Scientific Reports, 5: 10141, DOI: 10.1038/srep10141; Awitdrus, Deraman M, Talib I A, Farma R, Omar R, Ishak M M, Taer E, M. Dolah B N, Basri N H, Nor N S M, (2015) Physical and electrochemical properties of supercapacitor composite electrodes prepared from biomass carbon and carbon from green petroleum coke, The 5th Asian Physics Symposium (APS 2012), AIP Conf. Proc. 1656, 030007-1-030007-5, doi: 10.1063/1.4917096; Huang Y, Peng L, Liu Y, Zhao G, Chen J Y, Yu G, (2016) Bio-based Nano Porous Active Carbon Fibers for High-Performance Supercapacitors, ACS Appl. Mater. Interfaces, 8: 15205-15215; Mondal A K, Kretschmer K, Zhao Y, Liu H, Wang C, Sun B, Wang G, Nitrogen doped porous carbon nanosheets from eco-friendly *eucalyptus* leaves as high performance electrode materials for supercapacitors and lithium ion batteries, DOI: 10.1002/chem.201605019; Taer E, Deraman M, Talib I A, Awitdrus A, Hashmi S A, Umar A A, (2011) Preparation of a highly porous binder-less activated carbon monolith from rubber wood sawdust by a multi-step activation process for application in supercapacitors, Int. J. Electrochem. Sci., 6: 3301-3315; Xing L, Ma Z, (2016) A glassy carbon electrode modified with a nanocomposite consisting of $MoS_2$ and reduced graphene oxide for electrochemical simultaneous determination of ascorbic acid, dopamine, and uric acid, Microchim. Acta 183: 257-263; Chen J, He P, Bai H, Lei H, Zhang G, Dong F, Ma Y, (2016) A glassy carbon electrode modified with a nanocomposite consisting of carbon nano-horns and poly(2-aminopyridine) for non-enzymatic amperometric determination of hydrogen peroxide Microchim. Acta, 183: 3237-3242; Aziz M A, Yang H, (2007) Electro-chemical immunosensor using the modification of an amine-functionalized indium tin oxide electrode with carboxylated single-walled carbon nanotubes, Bull. Korean Chem. Soc., 28: 1171-1174; Zhang J, Zhong Z, Shen D, Zhao J, Zhang H, Yang M, Li W, (2011) Preparation of bamboo-based activated carbon and its application in direct carbon fuel cells, Energy Fuels, 25: 2187-2193]. These carbon materials are generally produced in the form of carbon nanoparticles/nanomaterials, e.g. carbon nanotubes, graphene nanoparticles, glassy carbon nano/microspheres, etc. because carbon nanoparticles possess a higher specific surface area than regular carbon materials, whereas the advantageous electrical and thermal conductivities and electrocatalytic and capacitive properties are retained. Several researchers have investigated the incorporation of carbon nanoparticles to working electrodes of electrochemical cells to modify the cell efficiency. However, incorporating (or adhering) carbon nanoparticles to the electrodes generally require the presence of an adhesive materials that hinders the electroactive surface of the electrode, and thus degrades electrochemical properties and cell efficiency [Taer E, Deraman M, Talib I A, Awitdrus A, Hashmi S A, Umar A A, (2011) Preparation of a highly porous binder-less activated carbon monolith from rubber wood sawdust by a multi-step activation process for application in supercapacitors, Int. J. Electrochem. Sci., 6: 3301-3315; Aziz M A, Yang H, (2007) Electro-chemical immunosensor using the modification of an amine-functionalized indium tin oxide electrode with carboxylated single-walled carbon nanotubes, Bull. Korean Chem. Soc., 28: 1171-1174]. In addition, producing carbon nanoparticles and adhering them onto an electrode substrate is generally an expensive process, particularly when the manufacturing cost is added to the cost of the electrode substrate, which is generally made from platinum, gold, palladium, and glassy carbon materials.

Micro/nanostructured carbon materials are widely produced from various types of biomass/agro-waste such as grass, coconuts, and/or rice husks by pyrolysis of the biomass followed by hydrothermal methods [M. S. Islam, M. A. Rouf, (2012) Waste biomass as sources for activated carbon production-A review, Bangladesh J. Sci. Ind. Res., 47: 347-364; Tan J S, Ani F N, (2004) Carbon molecular sieves produced from oil palm shell for air separation, Separation and Purification Technology, 35: 47-54; Ahmad T, Danish M, Rafatullah M, Ghazali A, Sulaiman O, Hashim R, Ibrahim M N M, (2012) The use of date palm as a potential adsorbent for wastewater treatment: a review, Environ Sci. Pollut. Res 19: 1464-1484; Meryemoglu B, Irmak S, Hasanoglu A, (2016) Fuel Processing Technology, 151: 59-63; Abioye A M, Ani F N, (2015) Recent development in the production of activated carbon electrodes from agricultural waste biomass for supercapacitors: A review, Renewable and Sustainable Energy Reviews, 52: 1282-1293; Veeramani V, Madhu R, Chen S-M, Lou B-S, Palanisamy J, Vasanth V S, (2015) Biomass-derived functional porous carbons as novel electrode material for the practical detection of biomolecules in human serum and snail hemolymph Scientific Reports, 5: 10141, DOI: 10.1038/srep10141; Awitdrus, Deraman M, Talib I A, Farmina R, Omar R, Ishak M M, Taer E, M. Dolah B N, Basri N H, Nor N S M, (2015) Physical and electrochemical properties of supercapacitor composite electrodes prepared from biomass carbon and carbon from green petroleum coke, The 5th Asian Physics Symposium (APS 2012), AIP Conf. Proc. 1656, 030007-1-030007-5, doi: 10.1063/1.4917096; Huang Y, Peng L, Liu Y, Zhao G, Chen J Y, Yu G, (2016) Bio-based Nano Porous Active Carbon Fibers for High-Performance Supercapacitors, ACS Appl. Mater. Interfaces, 8: 15205-15215; Mondal A K, Kretschmer K, Zhao Y, Liu H, Wang C, Sun B, Wang G, Nitrogen doped porous carbon nanosheets from eco-friendly *eucalyptus* leaves as high performance electrode materials for supercapacitors and lithium ion batteries, DOI: 10.1002/chem.201605019; Taer E, Deraman M, Talib I A, Awitdrus A, Hashmi S A, Umar A A, (2011) Preparation of a highly porous binder-less activated carbon monolith from rubber wood sawdust by a multi-step activation process for application in supercapacitors, Int. J. Electrochem. Sci., 6: 3301-3315; Zhang J, Zhong Z, Shen D, Zhao J, Zhang H, Yang M, Li W, (2011) Preparation of bamboo-based activated carbon and its application in direct carbon fuel cells, Energy Fuels, 25: 2187-2193; Nagaraju G, Lim J H, Cha S M, Yu J S, (2016) Three-dimensional Activated Porous Carbon with Meso/Macropore Structures Derived from Fallen Pine Cone Flowers: A Low-cost Counter Electrode Material in Dye-sensitized Solar Cells, Journal of Alloys and Compounds, DOI: 10.1016/j.jallcom.2016.10.015; Abioye A M, Ani F N, (2015) Recent development in the production of activated carbon electrodes from agricultural waste biomass for supercapacitors: A review, Renewable and Sustainable Energy Reviews 52: 1282-1293; Kang Z, Wang E, Mao B, Su Z, Chen L, Xu L, (2005) Obtaining carbon nanotubes from grass, Nanotechnology, 16: 1192-1195; Islam M A, Tan I A W, Benhouria A, Asif M, Hameed B H, (2015) Mesoporous and adsorptive properties of palm date seed activated carbon prepared via sequential hydrothermal carbonization and sodium hydroxide activation, Chemical Engineering Journal, 270: 187-195; Shoaib M, Hassan M, Al-Swaidan (2014) Effect of $CO_2$ Flow Rate on the Synthesis of Sliced Activated Carbon from Date Palm Tree Fronds (Agro-waste) by Physical Activation, Asian Journal of Chemistry, 26: 7025-7028; Alaya M N, B. S. Girgis, MOURAD W E, (2000) Activated Carbon from Some Agricultural Wastes Under Action of One-Step Steam Pyrolysis, Journal of Porous Materials, 7: 509-517; Flexer V, Donose B C, Lefebvre C, Pozo G, Boone M N, Hoorebeke L V, Baccour M, Bonnet L, Calas-Etienne S, Galarneau A, Titirici M M, Brun N, (2016) Microcellular Electrode Material for Microbial Bioelectrochemical Systems Synthesized by Hydrothermal Carbonization of Biomass Derived Precursors, ACS Sustainable Chem. Eng., 4: 2508-2516; Gao Z, Zhang Y, Song N, Li X, (2016) Biomass-derived renewable carbon materials for electrochemical energy storage, Mater. Res. Lett., doi:10.1080/21663831.2016.1250834; Ruan G, Sun Z, Peng Z, Tour J M, (2011) Growth of Graphene from Food Insects and Waste, ACS Nano, 5: 7601-7607; Saqib Shams S, Zhang L S, Hu R, Zhang R, Zhu J, (2015) Synthesis of graphene from biomass: A green chemistry approach, Materials Letters, 161: 476-479]. In some other investigations, agricultural waste biomass has been used to produce carbonaceous materials for adsorbing environmental pollutants [Ahmad T, Danish M, Rafatullah M, Ghazali A, Sulaiman O, Hashim R, Ibrahim M N M, (2012) The use of date palm as a potential adsorbent for wastewater treatment: a review, Environ Sci. Pollut. Res 19: 1464-1484; Islam M A, Tan I A W, Benhouria A, Asif M, Hameed B H, (2015) Mesoporous and adsorptive properties of palm date seed activated carbon prepared via sequential hydrothermal carbonization and sodium hydroxide activation, Chemical Engineering Journal, 270: 187-195; Shoaib M, Hassan M, Al-Swaidan (2014) Effect of $CO_2$ Flow Rate on the Synthesis of Sliced Activated Carbon from Date Palm Tree Fronds (Agro-waste) by Physical Activation, Asian Journal of Chemistry, 26: 7025-7028; Alaya M N, B. S. Girgis, MOURAD W E, (2000) Activated Carbon from Some Agricultural Wastes Under Action of One-Step Steam Pyrolysis, Journal of Porous Materials, 7: 509-517].

The agro-waste of date palm trees is very inexpensive, due to a large population of date palm trees particularly in tropical countries. However the carbon materials obtained from agro-waste is typically too irregularly structured and/or of incorrect/inconsistent particle size for effective use as an electrode material.

In view of the forgoing, one objective of the present disclosure is to provide an electrode that comprises a nanostructured material that includes pyrolyzed date palm leaves that are obtained from a pyrolysis of an agro-waste containing date palm leaves in an inert gas and in a temperature range of 800 to 1600° C. and which can effectively function without a separate substrate layer. Another objective of the present disclosure is to provide an electrochemical cell that utilizes the electrode as a working electrode. The present disclosure further relates to a method of determining a hydroquinone concentration in a hydroquinone-containing solution with the electrochemical cell.

BRIEF SUMMARY OF THE INVENTION

According to a first aspect, the present disclosure relates to an electrode comprising a nanostructured material that includes pyrolyzed date palm leaves that are obtained from a pyrolysis of an agro-waste containing date palm leaves in an inert gas and in a temperature range of 800 to 1600° C.

In one embodiment, the inert gas is selected from the group consisting of nitrogen, helium, neon, and argon.

In one embodiment, the agro-waste consists of date palm leaves.

In one embodiment, the nanostructured material is not disposed on a substrate.

In one embodiment, the electrode further includes a conductive material, wherein the nanostructured material is disposed on the conductive material with an adhesive.

In one embodiment, the nanostructured material has a thickness in the range of 10 to 1,000 μm.

In one embodiment, the nanostructured material further includes at least one element selected from the group consisting of oxygen, nitrogen, iron, silicon, potassium, and calcium.

In one embodiment, the nanostructured material has a BET surface area in the range of 150 to 300 $m^2/g$.

In one embodiment, the nanostructured material comprises carbon walls that are arranged in a stacked configuration.

In one embodiment, the nanostructured material is porous with an average pore size of 1 to 10 nm.

According to a second aspect, the present disclosure relates to an electrochemical cell including i) a working electrode comprising a nanostructured material that includes pyrolyzed date palm leaves that are obtained from a pyrolysis of an agro-waste containing date palm leaves in an inert gas and in a temperature range of 800 to 1600° C., ii) a reference electrode, iii) a counter electrode, wherein the reference electrode and the counter electrode are in ionic communication with the working electrode via an electrolyte.

In one embodiment, the electrolyte comprises hydroquinone.

In one embodiment, the reference electrode comprises silver-silver chloride.

In one embodiment, the counter electrode comprises platinum.

According to a third aspect, the present disclosure relates to a method of determining a hydroquinone concentration in a hydroquinone-containing solution with the electrochemical cell, the method involving i) contacting the hydroquinone-containing solution with the working electrode, the counter electrode, and the reference electrode of the electrochemical cell, ii) applying a voltage to the working electrode relative to the reference electrode to oxidize at least a portion of hydroquinone in the hydroquinone-containing solution thereby generating an electric current in the electrochemical cell, iii) determining the hydroquinone concentration in the hydroquinone-containing solution based on the electric current.

In one embodiment, a detection limit of the electrochemical cell is in the range of 1.0 to 10.0 μM of hydroquinone.

In one embodiment, the hydroquinone concentration in the hydroquinone-containing solution is in the range of 1.0 μM to 1.0 M.

In one embodiment, the hydroquinone concentration is determined at a temperature in the range of 10 to 40° C.

In one embodiment, the hydroquinone-containing solution includes hydroquinone and at least one of a halide, a sulfate, a nitrate, a phosphate, an acetate of an alkali metal, and nitrophenol.

In one embodiment, a hydroquinone selectivity of the electrochemical cell is at least 95% by mole.

In one embodiment, the voltage is in the range of 0.05 to 0.5 volts relative to the reference electrode.

In one embodiment, the hydroquinone concentration is determined from a calibration curve that linearly relates the electric current to the hydroquinone concentration.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 12A represents cyclic voltammograms of an electrochemical cell having a working electrode comprising the nanostructured material, which is obtained from the pyrolysis of date palm leaflets at (a) 850° C. and an electrolyte comprising 0.1 M KCl; and (b) 850° C. and an electrolyte comprising 0.1 M KCl and 5.0 mM $K_4[Fe(CN)_6]$.

FIG. 12B represents cyclic voltammograms of (a) an electrochemical cell having a glassy carbon electrode and an electrolyte comprising 0.1 M KCl; and (b) an electrochemical cell having a glassy carbon electrode and an electrolyte comprising 0.1 M KCl and 5.0 mM $K_4[Fe(CN)_6]$.

DETAILED DESCRIPTION OF THE EMBODIMENTS

Figure 1:
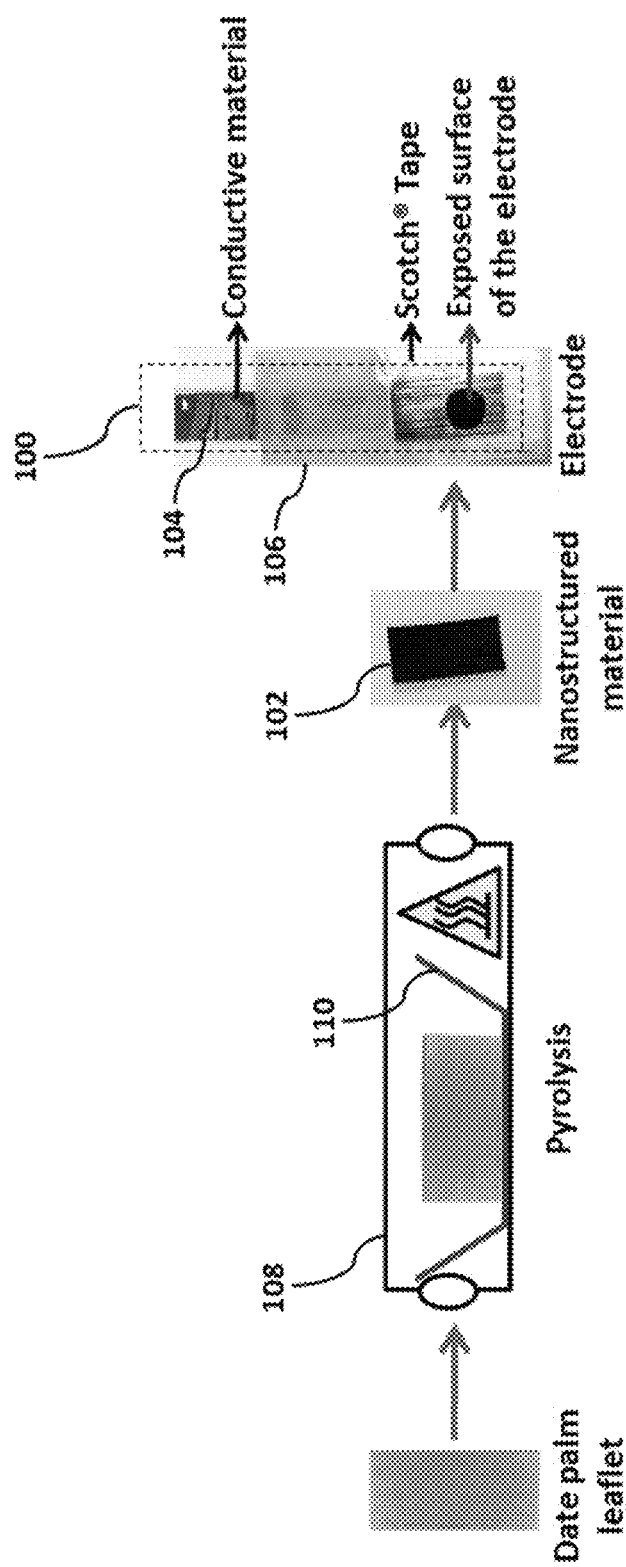
FIG. 1 schematically represents the steps of preparing an electrode, which is obtained from a pyrolysis of date palm leaflets.

Referring now to the drawings, wherein like reference numerals designate identical or corresponding parts throughout the several views.

Figure 7:
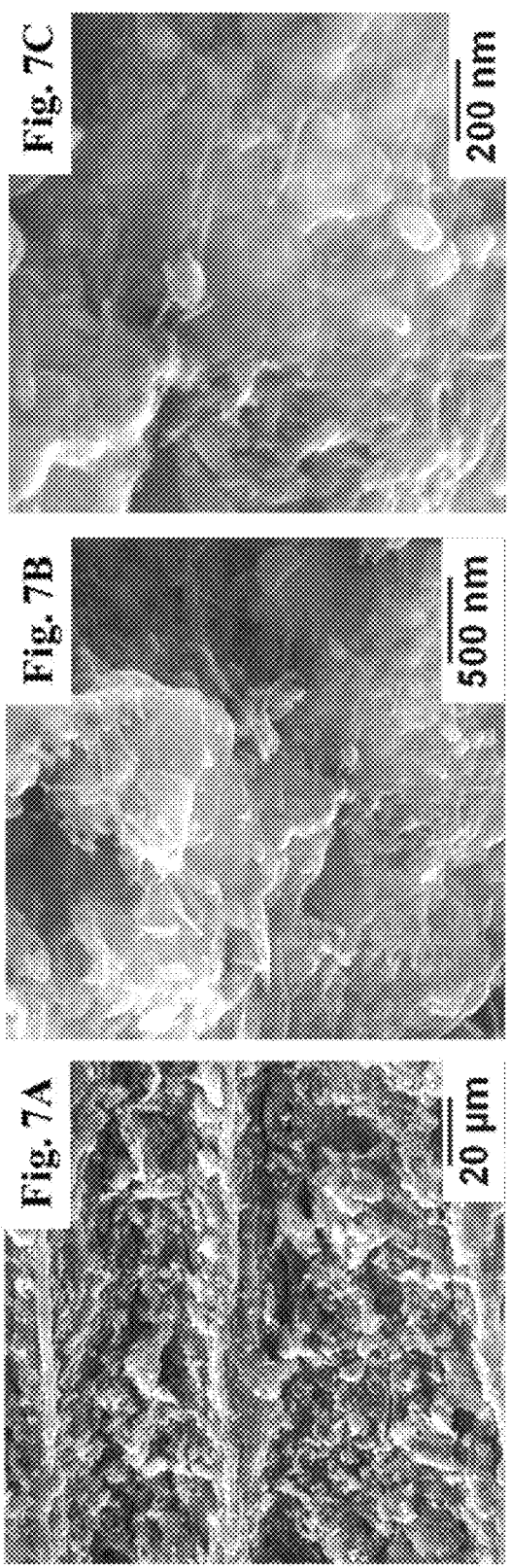
FIG. 7A is a SEM micrograph of the nanostructured material, which is obtained from the pyrolysis of date palm leaflets at 1,500° C.
FIG. 7B is a magnified SEM micrograph of the nanostructured material, which is obtained from the pyrolysis of date palm leaflets at 1,500° C.
FIG. 7C is high-magnified SEM micrograph of the nanostructured material, which is obtained from the pyrolysis of date palm leaflets at 1,500° C.
Figure 8:
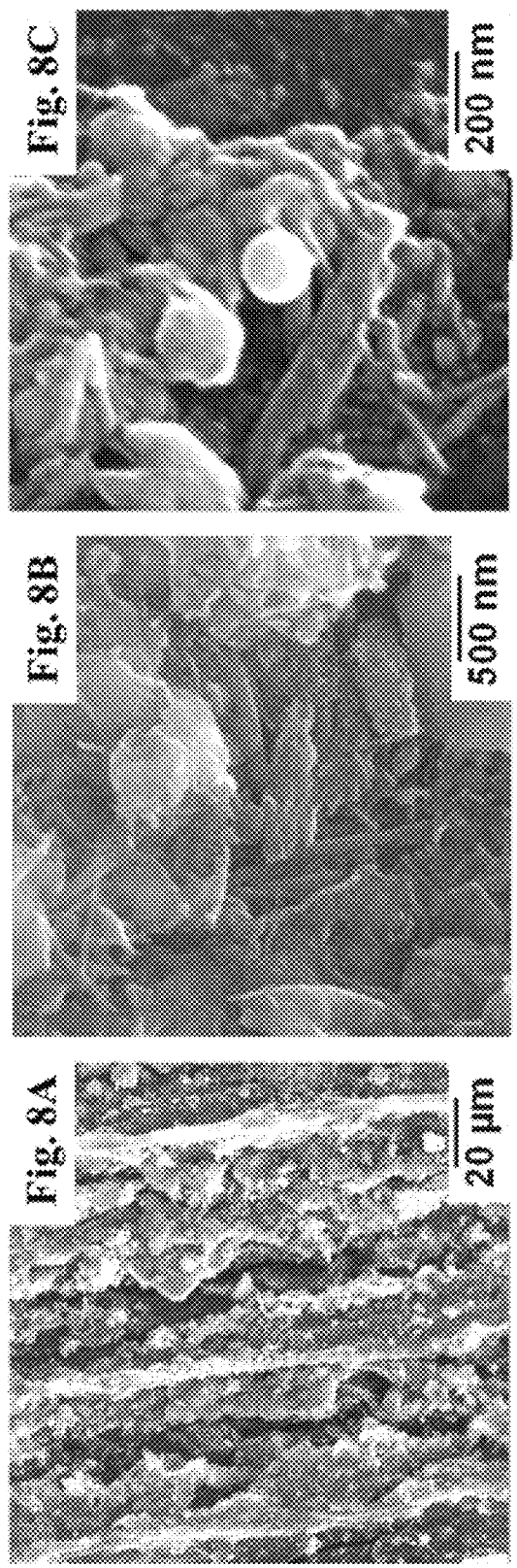
FIG. 8A is a SEM micrograph of the nanostructured material, which is obtained from the pyrolysis of date palm leaflets at 850° C.
FIG. 8B is a magnified SEM micrograph of the nanostructured material, which is obtained from the pyrolysis of date palm leaflets at 850° C.
FIG. 8C is high-magnified SEM micrograph of the nanostructured material, which is obtained from the pyrolysis of date palm leaflets at 850° C.

According to a first aspect, the present disclosure relates to an electrode 100 comprising a nanostructured material 102. The term "nanostructured material" as used in this disclosure relates to a carbonaceous (carbon-containing) material that includes carbon walls that are arranged in a stacked configuration (as shown in FIGS. 7A and 8A). Preferably, the presence of the carbon walls in the pyrolyzed date palm leaves (or preferably date palm leaflets) may distinguish the nanostructured material of this disclosure, which is obtained from the pyrolysis of date palm leaves (or preferably date palm leaflets), from other structured carbonaceous materials that are obtained from the pyrolysis of other agro-waste/biomass sources. Accordingly, as shown in FIGS. 7A and 8A, the carbon walls are porous carbon structures that may have a thickness ranging from about 1.0 to about 50 μm, preferably from about 2.0 to about 40 μm, preferably from about 5.0 to about 30 μm, preferably from about 10 to about 25 μm. The term "stacked configuration" as used herein refers to an arrangement, wherein the carbon walls are located parallel to one another thereby forming channels therebetween, wherein a width of the channels may range from about 10 to about 500 μm, preferably from about 20 to about 200 μm, preferably from about 40 to about 100 μm, and a depth of the channels may range from about 10 μm to about 1,000 μm, preferably from about 20 to about 800 μm, preferably from about 50 to about 500 μm, preferably from about 100 to about 400 μm. An aspect ratio (i.e. a ratio of length to width) of the carbon walls may range from about 1,000:1 to 1:1, preferably 500:1 to 2:1, preferably 100:1 to 10:1.

In some preferred embodiments, the nanostructured material contains pores with an average pore size in the range of 1 to 10 nm, preferably 1.5 to 5.0 nm, preferably 1.8 to 4.0 nm, preferably 2.0 to 2.5 nm; a specific pore volume in the range from about 0.1 to about 1.0 $cm^3/g$, preferably from about 0.3 to about 0.9 $cm^3/g$, preferably from about 0.5 to about 0.8 $cm^3/g$; and a BET surface area in the range from about 150 to about 300 $m^2/g$, preferably from about 160 to about 280 $m^2/g$, preferably from about 180 to about 250 $m^2/g$, preferably from about 190 to about 220 $m^2/g$.

Figure 9:
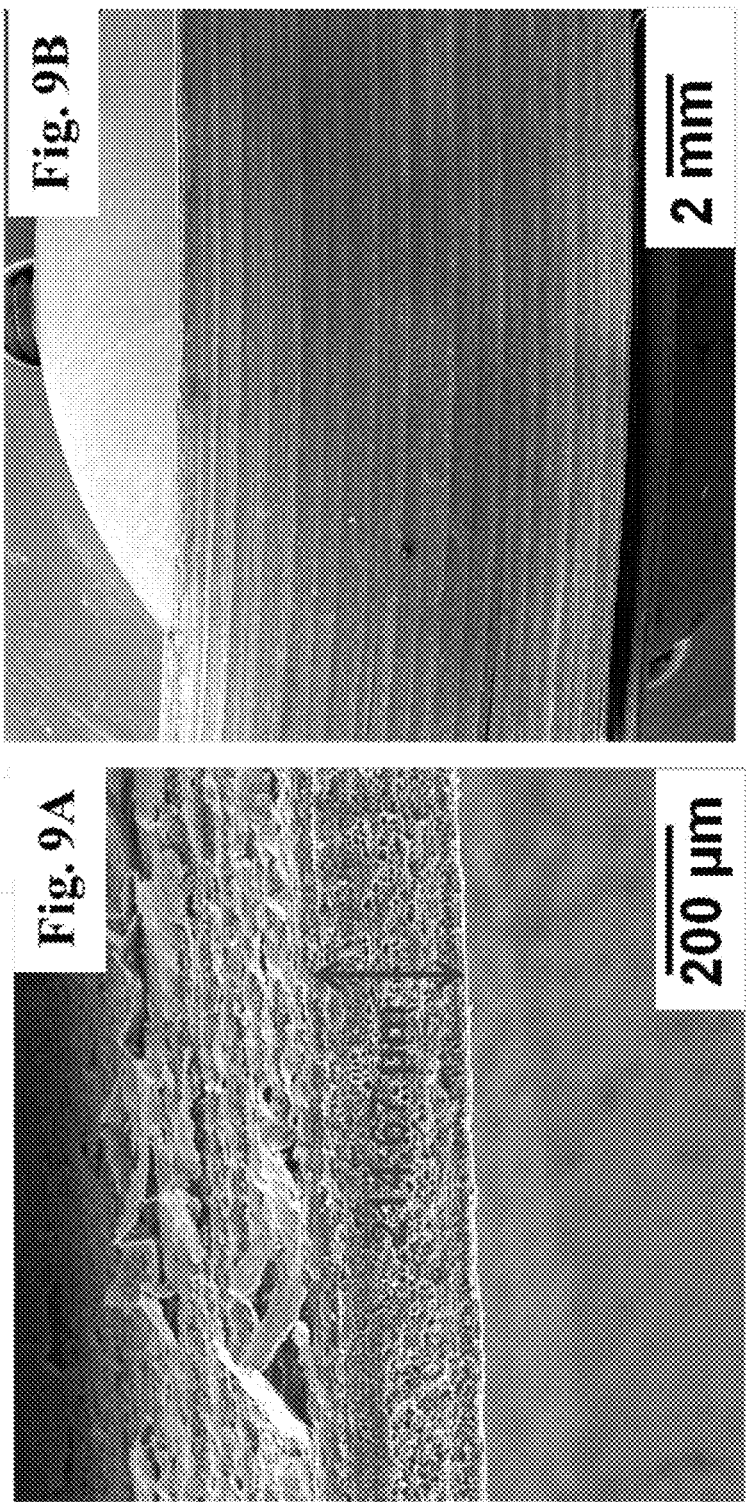
FIG. 9A is a side-view and low-magnified SEM micrograph of the nanostructured material, which is obtained from the pyrolysis of date palm leaflets at 850° C.
FIG. 9B is a top-view and low-magnified SEM micrograph of the nanostructured material, which is obtained from the pyrolysis of date palm leaflets at 850° C.

In a preferred embodiment, the nanostructured material 102 has a thickness in the range of 10 to 1,000 μm, preferably 50 to 800 μm, preferably 100 to 600 μm, preferably 150 to 500 μm, preferably 180 to 400 μm, preferably about 200 μm, as shown in FIG. 9A. The nanostructured material may have a plurality of carbon walls that are arranged in the stacked configuration, wherein each stack may contain at least 5 carbon walls, preferably at least 8 carbon walls, preferably at least 10 carbon walls, preferably 15 to 25 carbon walls.

The pores present in the nanostructured material 102 may be three-dimensionally interconnected via the carbon walls (as shown in FIGS. 7A, 7B, 8A, and 8B). The carbon walls are porous carbon structures, wherein a ratio of the average pore size of the carbon walls to the average pore size of the nanostructured material may be in the range of 1:10 to 1:1, preferably 1:6 to 1:2, preferably about 1:3. In addition, a ratio of the BET surface area of the carbon walls to the average pore size of the nanostructured material may be in the range of 1:10 to 1:1, preferably 1:6 to 1:2, preferably about 1:3. In view of that, the carbon walls of the nanostructured material are preferably less porous and hence more rigid when compared to the nanostructured material. Therefore, the presence of the carbon walls provides mechanical stability to the nanostructured material.

The nanostructured material 102 may be utilized in various applications due to light weight, mechanical stability, and relatively high electrical and thermal conductivities. Accordingly, the nanostructured material 102 may be utilized as an electrode in fuel cells, photovoltaic cells, electrochemical cell, and solar cells; as a drug carrier for drug-delivery applications, as an adsorbing material, as a catalyst carrier, as a heat-insulating material, as a buffer material, as a filter, as a tool in ceramic sintering, etc.

The nanostructured material 102 of this disclosure is obtained from a pyrolysis of an agro-waste containing date palm leaves in an inert gas, e.g. nitrogen, helium, neon, and/or argon, and in a temperature range of 800 to 1600° C., preferably 900 to 1,550° C., preferably 1,000 to 1,500° C., preferably 1,100 to 1,450° C., preferably 1,200 to 1,400° C. In a preferred embodiment, the nanostructured material 102 is obtained from a pyrolysis of an agro-waste containing date palm leaves in the presence of nitrogen gas and in a temperature in the range of 1,300 to 1,600° C., preferably about 1,500° C. In another embodiment, the nanostructured material 102 is obtained from a pyrolysis of an agro-waste containing date palm leaves in the presence of nitrogen gas and in a temperature in the range of 800 to 1,000° C., preferably about 850° C.

The term "inert gas" as used herein refers to a gaseous mixture that does not chemically react with the agro-waste during the pyrolysis. In a preferred embodiment, the inert gas is at least one selected from the group consisting of nitrogen, helium, neon, and argon. However, the inert gas is not limited to nitrogen, helium, neon, and/or argon; and other gaseous mixtures that do not react with the agro-waste during the pyrolysis may also be utilized.

The term "agro-waste" as used in this disclosure relates to any leftover or waste materials obtained from an agricultural product or process. Examples of agro-waste may include, but are not limited to residual plant materials such as husks, shells, stems, roots, leaves, leaflets, or cores. For example, in some embodiments, the agro-waste includes palm leaves (e.g. date palm leaves), soybean hulls, cellulosic fibers, cellulose, grass, coconut shells, rice husks, corn stalks, wheat straw, wood chips, and wood pulp that remains after wood processes (e.g., sawmills or lumber yards). Preferably, the agro-waste contains date palm wastes, e.g. trunks, pits, roots, stems, leaves, and/or leaflets of date palm trees. However, in a preferred embodiment, the agro-waste consists of date palm leaflets. According to this embedment, less than 1.0 vol %, preferably less than 0.5 vol %, preferably less than 0.1 vol % of the agro-waste that is utilized to form the nanostructured material contains trunks, pits, roots, and/or stems of date palm trees.

The nanostructured material 102 may have various compositions depending on the type of the agro-waste that is pyrolyzed. In some embodiments, the date palm leaves (or preferably date palm leaflets) comprises cellulose, hemicellulose, and lignin, wherein the amount of cellulose is at least 50 wt %, preferably in the range of 50 wt % to 70 wt %, preferably 55 wt % to 65 wt %, relative to the total weight of the date palm leaves. In addition, the date palm leaves (or preferably date palm leaflets) includes minerals such as iron, magnesium, silicon, potassium, and calcium. The composition of the date palm leaves may be different than the composition of other agro-waste, e.g. date palm trunk, date palm fronds, rice husk, etc. wherein the amount of cellulose is no more than 40 wt %, preferably no more than 30 wt %. In addition, the amount of minerals such as iron, magnesium, silicon, potassium, and calcium in these agro-wastes is at least 20%, preferably at least 40%, preferably at least 60% lower than that of the date palm leaves. According to the compositional difference, the nanostructured material, which is obtained from the pyrolysis of date palm leaves, may have a different composition than the composition of a material which is obtained from the pyrolysis of an agro-waste other than date palm leaves. For example, in one embodiment, the nanostructured material, which is obtained from date palm leaves (or preferably date palm leaflets) includes at least 90 wt %, preferably at least 95 wt % carbon as well as at least at least 5 wt %, preferably about 8 wt % to about 10 wt % (relative to the total weight of the nanostructured material) of a mineral selected from the group consisting of oxygen, nitrogen, iron, silicon, potassium, manganese, magnesium, and calcium; whereas a material that is obtained from the pyrolysis of date palm trunks, includes at least 95 wt %, or preferably at least 98 wt % carbon as well as about 2 wt %, preferably about 3 wt % to about 5 wt % of a mineral selected from the group consisting of oxygen, nitrogen, iron, silicon, and calcium. Said compositional differences may affect electrical properties, e.g. electrical conductivity, particular when the nanostructured material is used in an electrochemical cell.

The term "pyrolysis" as used in this disclosure refers to a process of thermochemical decomposition of an agro-waste at elevated temperatures and in the absence of an oxidizing agent such as oxygen, hydrogen peroxide, and/or a halogen-containing gas, e.g. a chlorine-containing gas. The agro-waste may have a polymeric structure consisting of carbohydrates (cellulose and hemicellulose) and lignin with small amounts of extraneous organic chemicals and minerals. The pyrolysis of the agro-waste may form a solid, for example in a form of ash, that mainly contains carbon atoms, heteroatoms (e.g. nitrogen, oxygen, and hydrogen), and minerals. The pyrolysis of the agro-waste may also form char, tar, and volatile compounds, which may evaporate during the pyrolysis thus leaving behind the nanostructured material 102.

In some embodiments, the agro-waste is pyrolyzed according to the following procedure. First, the agro-waste is placed in a ceramic crucible 110, e.g. an alumina crucible, and is heated to a temperature of 100 to 120° C., preferably about 105° C., for at least 24 hours, preferably at least 36 hours, but no more than 48 hours, to remove water from the agro-waste. Then, the agro-waste is heated with a heating rate in the range of 5 to 20° C./min, preferably 8 to 15° C./min, preferably about 10° C./min to an elevated temperature in the range of 800 to 1600° C., preferably 900 to 1,550° C., preferably 1,000 to 1,500° C., preferably 1,100 to 1,450° C., preferably 1,200 to 1,400° C., in an inert gas, preferably nitrogen. The agro-waste is isothermally heated at the elevated temperature for at least 2 hours, preferably at least 4 hours, but no more than 12 hours. All heating steps may be performed in a furnace 108 having a temperature control system, which may provide a heating rate of up to 50° C./min, or preferably up to 40° C./min, or preferably up to 30° C./min. The furnace 108 may also be equipped with a cooling accessory, which may provide a cooling rate of up to 20° C./min, or preferably up to 15° C./min, or preferably up to 10° C./min. Accordingly, the furnace 108 may be cooled with a cooling air stream, a liquid nitrogen stream, or a combination thereof.

In one embodiment, the agro-waste is heated in a multi-step heating protocol, e.g. a two-step heating protocol, wherein the agro-waste is heated to a first elevated temperature in a range of 400 to 600° C., preferably 450 to 550° C., with a first heating rate in the range of 5 to 20° C./min, preferably about 10° C./min. The agro-waste may be isothermally heated at the first elevated temperature for at least 1 hour, but no more than 4 hours. Then, the agro-waste is heated to a second elevated temperature in a range of 800 to 1,600° C., preferably 1,200 to 1,400° C., with a second heating rate in the range of 1 to 6° C./min, preferably 2 to 5° C./min. The agro-waste may be isothermally heated at the second elevated temperature for at least 2 hours, preferably at least 4 hours, but no more than 12 hours. After that, the agro-waste is cooled to room temperature (i.e. a temperature in the range of 20 to 30° C., preferably about 25° C.) with a cooling rate in the range of 2 to 10° C./min, preferably about 5° C./min. The multi-step heating protocol, i.e. the first and the second heating rates, the first and the second elevated temperatures, the cooling rate, etc., may determine the carbon wall thickness and also the number of carbon walls in each stack as well as the average pore size and the BET surface area of the nanostructured material 102 and the carbon walls. For example, the multi-step heating protocol, as described, may form a nanostructured material with an average pore size in the range of 1 to 10 nm, preferably 1.5 to 5.0 nm, preferably 1.8 to 4.0 nm, preferably 2.0 to 2.5 nm; and a BET surface area in the range from about 150 to about 300 $m^2/g$, preferably from about 160 to about 280 $m^2/g$, preferably from about 180 to about 250 $m^2/g$, preferably from about 190 to about 220 $m^2/g$. In addition, said multi-step heating protocol may form stacks of carbon walls, wherein each stack contains at least 5 carbon walls, preferably at least 8 carbon walls, preferably at least 10 carbon walls, preferably 15 to 25 carbon walls. The multi-step heating protocol may form carbon walls with a thickness ranging from about 1.0 to about 50 μm, preferably from about 2.0 to about 40 μm, preferably from about 5.0 to about 30 μm, preferably from about 10 to about 25 μm, and channels between the carbon walls, wherein the width of the channels may range from about 10 to about 500 μm, preferably from about 20 to about 200 μm, preferably from about 40 to about 100 μm, and a depth of the channels may range from about 10 μm to about 1,000 μm, preferably from about 20 to about 800 μm, preferably from about 50 to about 500 μm, preferably from about 100 to about 400 μm.

The term "electrode" as used in this disclosure relates to an electrical conductive material that brings into contact with a non-metallic element, e.g. an electrolyte, of a circuit, e.g. an electrochemical cell. Preferably, the term "electrode" in this disclosure refers to a working electrode of an electrochemical cell.

In some preferred embodiments, the agro-waste consists of date palm leaves having date palm leaflets. The date palm leaflets may preferably be separated from the date palm leaves and are cut into pieces having different sizes and shapes. For example, the date palm leaflets may cut into rounded pieces, circular pieces, elliptical pieces, and rectangular pieces, etc. Preferably, the date palm leaflets are cut into rectangular pieces (as shown in FIG. 1) with an aspect ratio (width to length ratio) in the range of 1:1 to 1:50, preferably 1:3 to 1:30, preferably 1:4 to 1:20, preferably 1:5 to 1:10, and a thickness of no more than 3 mm, preferably no more than 2 mm, preferably no more than 1 mm, preferably no more than 0.8 mm, preferably no more than 0.5 mm, preferably no more than 0.4 mm. The date palm leaflets that are cut into pieces may further be pyrolyzed to form the nanostructured material, which may be utilized as an electrode in an electrochemical cell without further processing. In a preferred embodiment, the nanostructured material 102 has a thickness in the range of 10 to 1,000 μm, preferably 50 to 800 μm, preferably 100 to 600 μm, preferably 150 to 500 μm, preferably 180 to 400 μm, preferably about 200 μm, as shown in FIG. 9A.

In a preferred embodiment, the nanostructured material 102 preserves its shape and stability at standard temperatures and pressures (i.e. a temperature in the range of 20 to 30° C., preferably 22 to 28° C., preferably about 25° C., and a pressure in the range of 0.8 to 1.2 atm, preferably 0.9 to 1.1 atm, and preferably about 1.0 atm). In view of that, the nanostructured material 102 may not be disposed on a substrate in applications that involves standard temperatures and pressures. For example, in one embodiment, the nanostructured material is utilized in an electrochemical cell that operates at standard temperatures and pressures, wherein the nanostructured material is not disposed on a substrate or a substrate electrode. The term "substrate" as used herein refers to a rigid material that provides stability to a material that is disposed thereon. Alternatively, the term "substrate" as used herein may refer to a carrier that carries a material that is disposed (or deposited) thereon. Accordingly, the nanostructured material is preferably not disposed (or secured) on a substrate such as glassy carbon, silicon wafer, glass, quartz, glass wafer, etc. However, the term "substrate" as used herein does not refer to a conductive material that is electrically in contact with the nanostructured material, wherein the conductive material is utilized as a junction to electrically connect the nanostructured material to a power source. In view of that, in one embodiment, the nanostructured material 102 is utilized in an electrochemical cell as an electrode, wherein the nanostructured material 102 is disposed on a conductive material 104 with an adhesive (not shown in FIG. 1). Preferably, the adhesive is conductive and may be selected from the group consisting of an alkyl acetate, a polyether acetate, a conductive epoxy, polythiophene, poly(thiophene-co-styrenesulfonate), polyaniline, polyacetylene, polypyrrole, and derivatives or combinations thereof. Preferably, the adhesive has a thickness of no more than 0.5 mm, preferably no more than 0.4 mm, preferably 0.1 to 0.3 mm. The conductive material 104 may be electrically connected to the nanostructured material 102 with methods known to the skilled in the art. In some embodiments, the conductive material 104 is selected from copper, gold, titanium, platinum, silver, palladium, ruthenium, rhenium, iron, nickel, indium, lead, tin, zinc, or combinations or alloys thereof. In a preferred embodiment, the conductive material 104 is copper or a copper alloy.

In a preferred embodiment, the cost of manufacturing the electrode 100 is substantially lower than the cost of manufacturing an electrode that includes carbon nanoparticles, e.g. carbon nanotubes, graphene sheets, fullerene, glassy carbon nano/microspheres, etc. deposited onto a conductive substrate, e.g. gold, platinum, palladium, glassy carbon, etc. Accordingly, the cost of manufacturing the electrode 100 may be at least two times, preferably at least three times, preferably at least five times lower than the cost of manufacturing an electrode that includes carbon nanoparticles deposited onto a conductive substrate.

Figure 2:
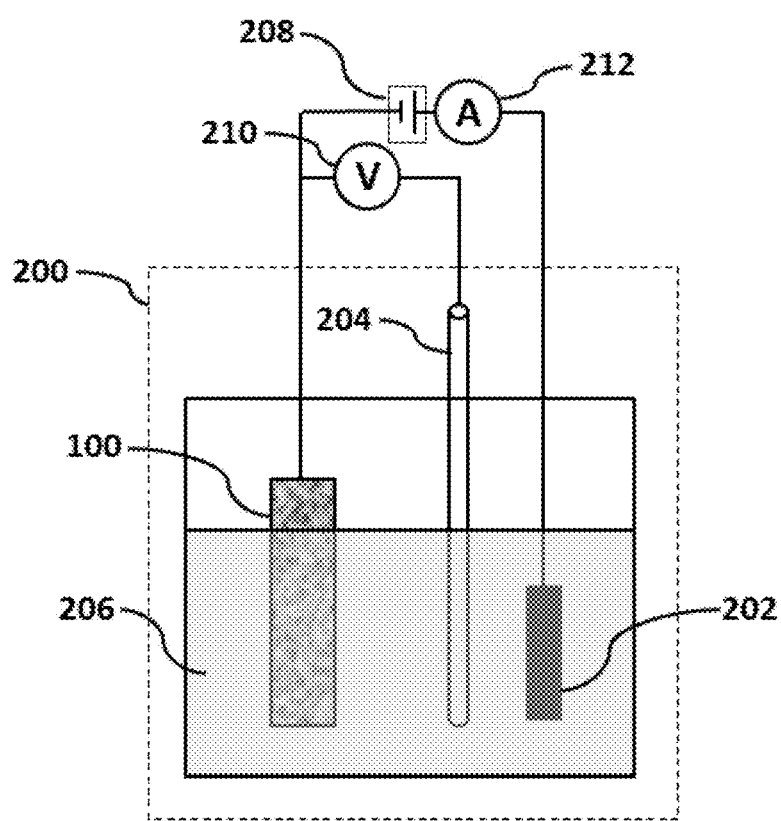
FIG. 2 is a schematic representation of an electrochemical cell, wherein a working electrode is obtained from a pyrolysis of date palm leaflets.

Referring now to FIG. 2, according to a second aspect, the present disclosure relates to an electrochemical cell 200 that includes a working electrode 100, a reference electrode 204, a counter electrode 202, and an electrolyte 206, wherein the reference electrode 204 and the counter electrode 202 are in ionic communication with the working electrode 100 via the electrolyte 206.

The electrochemical cell 200 provided in this disclosure may be utilized as an indicative tool to detect and/or determine a concentration of organic molecules such as hydroquinone and ferrocyanide, as well as bis-phenolic compounds such as bisphenol-A, bisphenol-F, bisphenol-S, bisphenol-C, bisphenol-E, bisphenol-P, bisphenol-Z, etc. In a preferred embodiment, the electrochemical cell 200 is utilized to detect and/or determine a concentration of hydroquinone in a solution. The electrochemical cell 200 provided herein may also be used to detect environmental pollutants or organic pesticides such as organophosphate.

The term "working electrode" as used in the second aspect refers to the term "electrode" as described in the first aspect. The term "working electrode" refers to the electrode when describing the specification of the electrochemical cell. Other than that, the term "electrode" and the term "working electrode" are identical and may be used interchangeably in this disclosure.

In some embodiments, the working electrode 100 includes the nanostructured material, which is obtained from the pyrolysis of the agro-waste. The working electrode 100 may further include the conductive material that is adhered to the nanostructured material from one side preferably with the adhesive. The conductive material may cover at least 10%, preferably at least 20%, preferably at least 30%, preferably at least 40%, preferably at least 50%, preferably at least 60%, preferably at least 70%, preferably at least 80%, preferably at least 90%, preferably at least 95%, preferably at least 99% of the surface area of one side of the nanostructured material. The conductive material may have a thickness in the range of 0.1 to 5 mm, preferably 0.5 to 3 mm, preferably 1 to 2 mm, whereas the adhesive may have a thickness of no more than 0.5 mm, preferably no more than 0.4 mm, preferably 0.1 to 0.3 mm. The working electrode 100 may or may not include the conductive material and/or the adhesive. The conductive material may only be used to electrically connect the nanostructured material to a power source, and is preferably not meant to take part in oxidizing the electrolyte. Accordingly, a volume ratio of the nanostructured material to the conductive material, when present, may be in the range of 1:1 to 1:20, preferably 1:1.5 to 1:15, preferably 1:2 to 1:12, preferably 1:2.5 to 1:10, preferably 1:3 to 1:8.

An electrical conductivity of the working electrode 100 may be within the range of $10^3$ to $3.0 \times 10^3$ s/m, preferably $1.2 \times 10^3$ to $2.5 \times 10^3$ s/m, preferably $1.5 \times 10^3$ to $2.0 \times 10^3$ s/m, at a temperature in the range of 20 to 30° C., preferably 22 to 28° C., preferably about 25° C.

In some embodiments, the working electrode 100 may further include an insulating material 106 which covers at least a portion of the nanostructured material (as shown in FIG. 1). The insulating material 106 may be utilized to create a specific surface area of the nanostructured material 102, which is exposed to the electrolyte 206. For example, in some embodiments, a pressure-sensitive adhesive such as Scotch Tape® is used to provide a circular surface area of the nanostructured material 102 that is exposed to the electrolyte 206. Exemplary insulating materials include, but are not limited to rubber, epoxy, poly acrylates, vinyl ester, methacrylates, etc. Said surface area may be rounded, e.g. elliptical, rectangular, square, triangular, star-shaped, etc.

In some embodiments, the nanostructured material 102 is coated with metallic nanoparticles before being used as the working electrode in the electrochemical cell. Preferably, the nanostructured material 102 is coated with metallic nanoparticles via deposition methods known to those skilled in the art, such as, e.g., sputtering, ion bombardment, etc. Preferably both sides of the nanostructured material are coated, although in some embodiments, only one side of the nanostructured material may be coated. Accordingly, in some embodiments, at least 10%, preferably at least 20%, preferably 50% to 100%, preferably 60% to 99.9%, preferably 80% to 99.5% of the surface area of the nanostructured material is coated with the metallic nanoparticles. The nanostructured material may be acid treated before being coated with the metallic nanoparticles thereon. Treating the nanostructured material with an acid, e.g., sulfuric acid and/or nitric acid may form carboxylic acid functional groups in the nanostructured material that may stabilize the metallic nanoparticles on the nanostructured material after coating, due to the presence of strong interactions between the metallic nanoparticles and carbon atoms that is provided via carboxylate groups.

The metallic nanoparticles may include, without limitation, copper, gold, titanium, platinum, silver, palladium, ruthenium, rhenium, iron, nickel, indium, lead, tin, zinc, or combinations thereof. The metallic nanoparticles may have an average particle size of less than 100 nm, preferably 10 to 80 nm, preferably 15 to 50 nm, more preferably 20 to 40 nm. In some embodiments, the metallic nanoparticles include bimetallic composite particles such as Pt—Ru, Pt—Ni, etc. The metallic nanoparticles may have similar rounded shapes, or may have various shapes including, without limitation, spherical, elliptical, cubical, hexagonal, pyramidal, conical, and/or irregular shapes. A coating layer may be formed after coating the nanostructured material with the metallic nanoparticles. A thickness of the coating layer may preferably be in the range from about 1 nm to 1 µm, preferably 2 to 500 nm, preferably 5 to 200 nm, preferably 10 to 100 nm, preferably 15 to 50 nm. The presence of the metallic nanoparticles in a form of the coating layer may enhance stability and may prolong an effective life span of the working electrode. In a preferred embodiment, an electrical conductivity of the working electrode, after coating with the metallic nanoparticles, is increased by at least 10%, preferably at least 20%, preferably at least 50%, preferably at least 80%, preferably at least 100%, preferably 120% to about 150%, relative to the electrical conductivity of the working electrode that is not coated with the metallic nanoparticles.

In one embodiment, the counter electrode 202 of the electrochemical cell 200 includes platinum. The counter electrode 202 may be made of platinum, or alternatively may be made of a platinum alloy including at least 50 wt %, preferably at least 60 wt %, preferably at least 70 wt %, preferably at least 80 wt %, preferably 85 wt % to 95 wt % relative to the total weight of the counter electrode. The counter electrode 202 may also include at least one metallic element selected from the group consisting of copper, gold, titanium, silver, palladium, ruthenium, rhenium, iron, nickel, indium, lead, tin, zinc. A weight ratio of the at least one metallic element to platinum in the counter electrode 202 is in the range from about 1:1 to about 1:20, preferably 1:2 to about 1:15, preferably 1:3 to about 1:12, preferably 1:5 to about 1:10. An electrical conductivity of the counter electrode 202 may be within the range of $3.0 \times 10^6$ to $7.0 \times 10^7$ s/m, preferably $5.0 \times 10^6$ to $5.0 \times 10^7$ s/m, preferably $10^7$ to $2.0 \times 10^7$ s/m, at a temperature in the range of 20 to 30° C., preferably 22 to 28° C., preferably about 25° C.

The reference electrode 204 as used herein is preferably stable over time and in various temperatures, i.e. the reference electrode 204 has a fixed and a reproducible electrode potential. The reference electrode 204 may be a saturated calomel electrode or preferably a silver/silver-ion electrode. In a preferred embodiment, the reference electrode 204 is a silver/silver-chloride electrode. The electrochemical cell may not include a reference electrode, and therefore the counter electrode may serve as a combined counter/reference electrode.

The working electrode 100, the reference electrode 204, and the counter electrode 202 are disposed adjacent to one another in the electrochemical cell 200 (as shown in FIG. 2) such that a gap is present between said electrodes, and a gap size may ranges from 0.5 cm to about 20 cm, preferably 0.8 to 10 cm, preferably 1.0 to 5.0 cm.

In one embodiment, the working electrode 100, the reference electrode 204, and the counter electrode 202 are in ionic communication via the electrolyte 206. The electrolyte 206 is an aqueous solution that includes hydroquinone, and may further include a halide, a sulfate, a nitrate, a phosphate, and an acetate of an alkali metal, phenol, a nitro-phenol and an amino-phenol, a bis-phenolic compound such as bisphenol-A, bisphenol-F, bisphenol-S, bisphenol-C, bisphenol-E, bisphenol-P, bisphenol-Z, etc. For example, in one embodiment, the electrolyte 206 includes hydroquinone and also includes potassium chloride, sodium sulfate, sodium phosphate, potassium nitrate, 2-nitrophenol, and 4-nitrophenol. The electrolyte 206 may have a pH in the range of 5 to 9, preferably 6 to 8, preferably about 7. In a preferred embodiment, when a voltage is applied to the working electrode 100 relative to the reference electrode 204, at least a portion of hydroquinone present in the electrolyte 206 is oxidized thereby generating an electric current in the electrochemical cell.

According to a third aspect, the present disclosure relates to a method of determining a hydroquinone concentration in a hydroquinone-containing solution with the electrochemical cell.

The hydroquinone-containing solution as used herein refers to an aqueous solution that contains hydroquinone (1,4-hydroquinone) and may further contain one or more of a halide, a sulfate, a nitrate, a phosphate, and/or an acetate of an alkali metal or an alkaline earth metal such as, e.g., potassium chloride, sodium sulfate, sodium phosphate, and potassium nitrate, phenol, a nitro phenol, e.g., 2-nitrophenol and 4-nitrophenol, an amino phenol, a bis-phenolic compound such as bisphenol-A, bisphenol-F, bisphenol-S, bisphenol-C, bisphenol-E, bisphenol-P, and bisphenol-Z, an alkoxy phenol compound such as methoxy phenol and ethoxy phenol, and an alcohol compound such as methanol, ethanol, propanol, isobutanol, n-butanol, and n-pentanol. In one embodiment, the hydroquinone-containing solution may be tap water, seawater, wastewater, bottled water, or water from a river, a lake, a pond, etc. In another embodiment, the hydroquinone-containing solution may be a blood sample. Preferably, the hydroquinone concentration in the hydroquinone-containing solution is within the range of 1.0 µM to 1.0 M, preferably 10 µM to 10 mM, preferably 20 µM to 10 mM, preferably 30 µM to 1.0 mM, preferably 40 µM to 500 µM. The preferable ranges of the hydroquinone concentration are not limited, and the method may determine the hydroquinone concentration when falls outside these preferable ranges. Also, the hydroquinone-containing solution may have a pH in the range of 5 to 9, preferably 6 to 8, preferably about 7.

The method may detect the presence of hydroquinone in a solution. The term "detect" as used herein refers to a qualitative measurement whereby the presence of hydroquinone in a solution is indicated. Also, the term "determine" as used in this disclosure relates to a quantitative measurement whereby a hydroquinone concentration is measured. In one embodiment, a detection limit of the electrochemical cell is in the range of 1.0 to 10.0 µM, preferably 2.0 to 8.0 µM, preferably 3.0 to 7.0 µM, preferably 4.0 to 6.0 µM of hydroquinone. The term "detection limit" as used herein refers to the smallest hydroquinone concentration that is detectable by the electrochemical cell. In another embodiment, the detection limit of the electrochemical cell is less than 1.0 µM, preferably in the range of 10 to 500 nM, preferably 50 to 200 nM.

According to the method, the hydroquinone-containing solution is first contacted with the working electrode, the counter electrode, and the reference electrode of the electrochemical cell. The hydroquinone-containing solution may preferably be contacted with the working electrode, the counter electrode, and the reference electrode for example by submerging (or partially submerging) said electrodes into the hydroquinone-containing solution (as shown in FIG. 2).

When the hydroquinone-containing solution is brought into contact with the working electrode, the counter electrode, and the reference electrode, a voltage is applied to the working electrode. The voltage is measured relative to the reference electrode 204 or a combined counter/reference electrode, e.g. in the embodiments where the electrochemical cell does not include reference electrode, with a voltmeter 210. In a preferred embodiment, the voltage is applied by a power source 208 that provides a DC current and the voltage is in the range of 0.05 to 0.5 volts, preferably 0.1 to 0.45 volts, preferably 0.2 to 0.4 volts, preferably about 0.3 volts, relative to the reference electrode, when the reference electrode is a silver/silver-chloride electrode. The voltage may also be outside of the above preferred ranges, e.g., in the range of 0.5 to 5.0 volts, or 1.0 to 4.0 volts, relative to the reference electrode. Accordingly, at least a portion of hydroquinone present in the hydroquinone-containing solution is oxidized on the working electrode. As a result, an electric current is generated in the electrochemical cell, which may be measured with an ammeter 212. The hydroquinone concentration may further be determined from the electric current via a calibration curve that correlates the electric current to the hydroquinone concentration.

Figure 17:
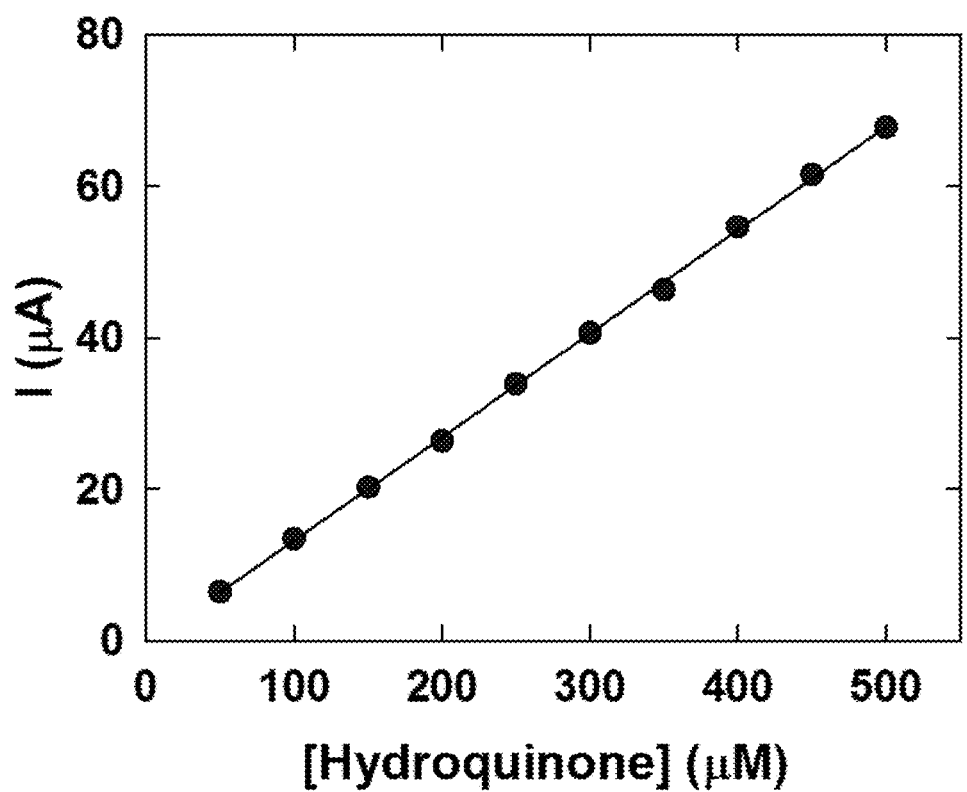
FIG. 17 represents a correlation curve between a hydroquinone concentration of an electrolyte and an electric current, which is generated due to an oxidation of a portion of hydroquinone in the electrolyte.

For example, in some embodiments, the electric current is linearly correlated to the hydroquinone concentration (as shown in FIG. 17), and the calibration curve may have a general formula as represented by equation (I):

$$[HQ] = a*I + b \tag{I}$$

wherein "[HQ]" represents a molar concentration of hydroquinone (in µM), "I" represents the electric current (in µA), "a" represents a constant value in the range of 2 to 10 $\mu M \cdot \mu A^{-1}$, preferably 4 to 9 $\mu M \cdot \mu A^{-1}$, preferably 6 to 8 $\mu M \cdot \mu A^{-1}$, preferably about 7.3 $\mu M \cdot \mu A^{-1}$, and "b" represents a constant value in the range of 1 to 5 µM, preferably 2 to 4 µM, preferably about 3.1 µM.

The calibration curve may depend on several characteristics of the electrochemical cell, for example, the electrical conductivity of each of the working electrode and the counter electrode, the pore size and the BET surface area of the working electrode, the pH of the electrolyte, a dielectric constant of the electrolyte, a temperature at which the hydroquinone concentration is determined, etc. In one embodiment, the hydroquinone concentration is determined at a temperature in the range of 10 to 40° C., preferably 15 to 35° C., preferably 20 to 30° C., preferably about 25° C.

In one embodiment, a response time of the electrochemical cell to determine the hydroquinone concentration is in the range of 5 to 60 seconds, preferably 10 to 30 seconds, preferably 12 to 20 seconds. The term "response time" as used herein refers to the time duration that is measured from contacting the hydroquinone-containing solution with the working electrode, the counter electrode, and the reference electrode until the hydroquinone concentration is determined.

In some embodiments, the hydroquinone-containing solution includes hydroquinone and one or more of a halide, a sulfate, a nitrate, a phosphate, and/or an acetate of an alkali metal or an alkaline earth metal such as, e.g., potassium chloride, sodium sulfate, sodium phosphate, and potassium nitrate, phenol, a nitro-phenol, e.g., 2-nitrophenol and 4-nitrophenol, an amino-phenol, an alkoxy phenol compound, e.g., methoxy phenol and ethoxy phenol, and an alcohol compound, e.g., methanol, ethanol, propanol, isobutanol, n-butanol, and n-pentanol; however, the hydroquinone-containing solution does not include the bis-phenolic compounds such as bisphenol-A, bisphenol-F, bisphenol-S, bisphenol-C, bisphenol-E, bisphenol-P, and bisphenol-Z. According to these embodiments, a hydroquinone selectivity of the electrochemical cell is at least 95% by mole, preferably at least 96% by mole, preferably at least 97% by mole, preferably at least 98% by mole, preferably at least 99% by mole. In the embodiments wherein the bis-phenolic compounds are present in the hydroquinone-containing solution, the hydroquinone selectivity of the electrochemical cell may be related to a molar ratio of the bis-phenolic compounds to hydroquinone. For example, in one embodiment, a molar ratio of the bis-phenolic compounds to hydroquinone is in the range of 1:1 to 1:5, preferably 1:1.5 to 1:4, preferably 1:2 to 1:3, wherein the hydroquinone selectivity of the electrochemical cell is in the range of 50% to 85% by mole, preferably 60% to 80% by mole, preferably 70% to 75% by mole. As used herein, the term "hydroquinone selectivity" refers to a molar ratio of hydroquinone relative to other organic molecules present in the hydroquinone-containing solution that are oxidized in the working electrode. For example, when the hydroquinone selectivity of the electrochemical cell is 95% by mole it means 95% by mole of all molecules that are oxidized in the working electrode is hydroquinone. The hydroquinone selectivity of the electrochemical cell may be related to the BET surface area and the pore size of the working electrode. Further, the hydroquinone selectivity may be related to the kinetics of oxidation. For example, at a specified voltage, hydroquinone may be more readily adsorbed onto the working electrode than other organic molecules present in the electrolyte.

The examples below are intended to further illustrate protocols for the electrode, the electrochemical cell, and the method of determining the hydroquinone concentration with the electrochemical cell, and are not intended to limit the scope of the claims.

EXAMPLE 1

Materials and Preparation of a Nanostructured Carbon Electrode (NSCE) from Date Palm Leaflets (DPLs)

Dead date palm leaves were collected from the lake side of King Fahd University of Petroleum and Minerals, Saudi Arabia. $N_2$ gas with a purity of 99.99% was supplied by the SCG gas center, Jubail, Kingdom of Saudi Arabia. Copper tape (one-sided adhesive) and Scotch 898 premium-grade Filament Tape (one-sided adhesive) were obtained from 3M, United States. Potassium chloride (KCl), potassium nitrate ($KNO_3$), sodium sulfate ($Na_2SO_4$), sodium phosphate monobasic monohydrate, sodium phosphate dibasic heptahydrate, acetic acid, sodium acetate, potassium ferrocyanide ($K_4[Fe(CN)_6]$), potassium ferricyanide ($K_3[Fe(CN)_6]$), and hydroquinone (HQ) were purchased from Sigma-Aldrich. 2-Nitrophenol and 4-nitrophenol were purchased from Fluka and Alfaser, respectively. De-ionized water was used throughout the experiments and was obtained by using a water purification system (Barnstead Nanopure, Thermo Scientific, USA).

Initially, the dead date palm leaves were washed with water and dried at 40° C. The leaflets from the leaves were separated and cut into 2-cm-long pieces. These pieces were placed in a flat alumina crucible, which was then inserted in the glass tube of a tubular furnace. We confirmed the position of the crucible in the middle of the tubular furnace. Next, we locked the glass tube and flushed in copious amounts of $N_2$ for five minutes to make an inert atmosphere. Next, we purged $N_2$ through the tube drop by drop, and commenced heating at a rate of 10° C./min until the temperature reached 850° C. The temperature was then maintained at this value for five hours. Next we cooled the furnace to room temperature (at a cooling rate of 5° C./min) and took out the prepared nanostructured carbon electrode (NSCE). The prepared NSCE is referred to as "$NSCE_{850}$" in this disclosure. The prepared $NSCE_{850}$ was made into a usable electrode by attaching copper tape to one side of it. Next, we covered $NSCE_{850}$ and the copper tape with the Scotch tape except for a 0.2 cm² area of the NSCE (working electrode area) and end of copper tape which were used to connect them with the potentiostat. The detailed procedure is described diagrammatically in FIG. 1.

EXAMPLE 2

Characterization Methodology

All electrochemical measurements were taken using a CHI (760E) electrochemical workstation (http://www.chinstruments.com). The prepared NSCE (working electrode area 0.2 cm²) or a 3-mm-diameter glassy carbon electrode (GCE) (working electrode area 0.071 cm²) was used as the working electrode, Ag/AgCl was used as the reference electrode, and a platinum wire was used as the counter electrode. The working surface area of the NSCE was 2.82 times greater than that of the GCE in the electrochemical experiments. We therefore multiplied the current obtained at the GCE by 2.82 to compare it to the current obtained at the NSCE." All electrochemical experiments were carried out at RT without de-aeration. FE-SEM images were obtained using a field emission scanning electron microscope (TESCAN LYRA 3, Czech Republic). Energy dispersive X-ray spectra (EDS) were recorded using an Xmass detector, Oxford Instruments, equipped with the Lyra3 TESCAN FESEM. TGA-DSC analysis was performed using a Netzsch STA (Model STA 449 F3). A Raman spectrometer (iHR320 with CCD detector, HORIBA) with green laser (300 mW) excitation at $\lambda_0$=532 nm was used to examine the graphite structure of the prepared NSCE. An XPS equipped with an Al-Kα micro-focusing X-ray monochromator (ESCALAB 250Xi XPS Microprobe, Thermo Scientific, USA) was applied for the chemical analysis of the prepared NSCE.

Brauner-Emmet-Teller (BET) nitrogen adsorption-desorption isotherms, and Barrett-Joyner-Halenda (BJH) methods were followed for analyzing specific surface area and pore size distribution, respectively by using (BET, Micromeritics ASAP 2020) at 77 K.

EXAMPLE 3

Thermal Analysis of NSCE

Figure 3:
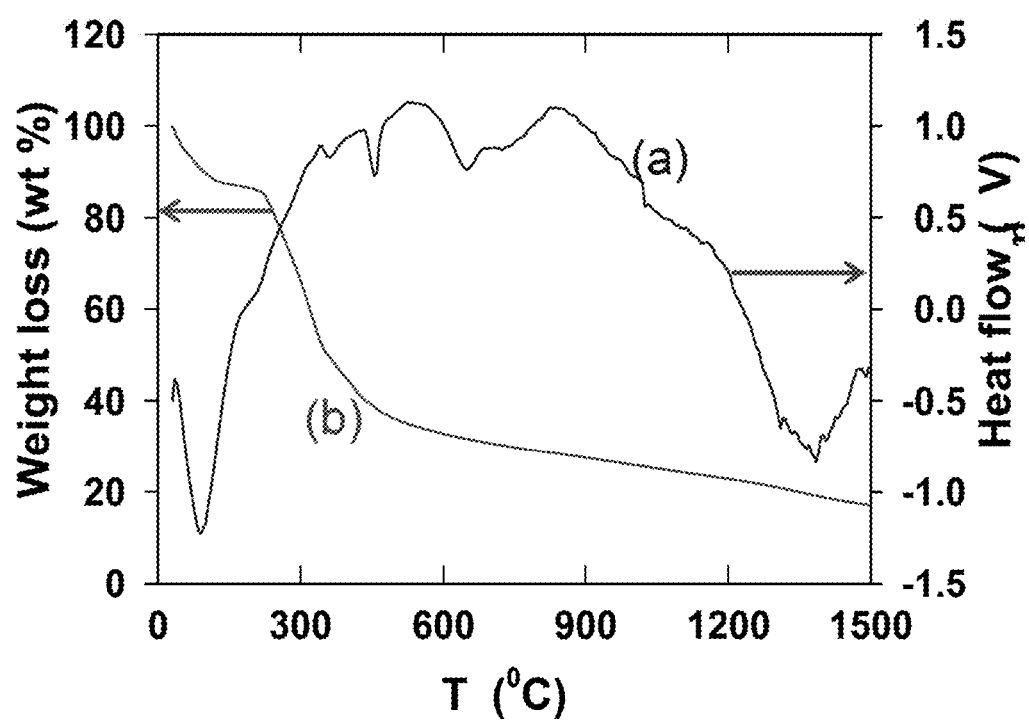
FIG. 3 (a) represents a differential scanning calorimetry (DSC) thermogram of date palm leaflets; (b) represents a thermogravimetric thermogram of the date palm leaflets.

FIGS. 3(a) and 3(b) show the DSC and TGA spectra of the date palm leaflets (DPLs), respectively. TGA-DSC analysis was performed with a scanning rate of 15° C./min from room temperature up to 1500° C. High-purity argon gas was continuously flowed through the calorimeter chamber at a rate of 20 ml/min to have the heating occur in an inert atmosphere. In the DSC spectrum (FIG. 3(a)), the major endothermic peaks that appeared were at 90, 360, 460, 650, and 1395° C. The first peak at 90° C. was associated with the decomposition of low-boiling-point organic molecules. The peaks at 360 and 460° C. may have resulted from the decomposition of hemicellulose and cellulose, and that at 650° C. from the decomposition of lignin to carbon. The last DSC peak, at 1395° C., may have arisen from the graphitization of amorphous carbon, which was generated at lower temperature. Possibility of the formation of graphite from this type of temperature treatment is discussed in detail in the Raman section.

The TGA curve (FIG. 3(b)) showed two sharp weight loss zones, one from 30 to 130° C. and the other from 210 to 480° C. About 12.25% of the initial weight of the sample was lost during the heating up to 130° C., which may have resulted from the loss of water molecules as well as the decomposition/loosing of low-boiling-point organic molecules, which was also suggested to occur in the DSC analysis. The sharp weight loss between 210 and 480° C. may have been due to the decomposition of hemicellulose and cellulose, as suggested in the DSC analysis. The obtained weight at 480° C. was 37% of that of the original sample. Upon increasing the temperature further, the weight of the sample decreased slowly. This additional weight loss may have been due to the decomposition of lignin and the graphitization of amorphous carbon (see also DSC analysis). The obtained weights at 850 and 1500° C. were 28.3 and 17.5% of the original DPL samples, respectively. The DPL sample was initially brown as indicated above, but turned black after the TGA treatment from 30 to 1500° C. This carbon obtained after the TGA treatment is referred to as "$NSCE_{1500}$" in this disclosure.

Figure 4:
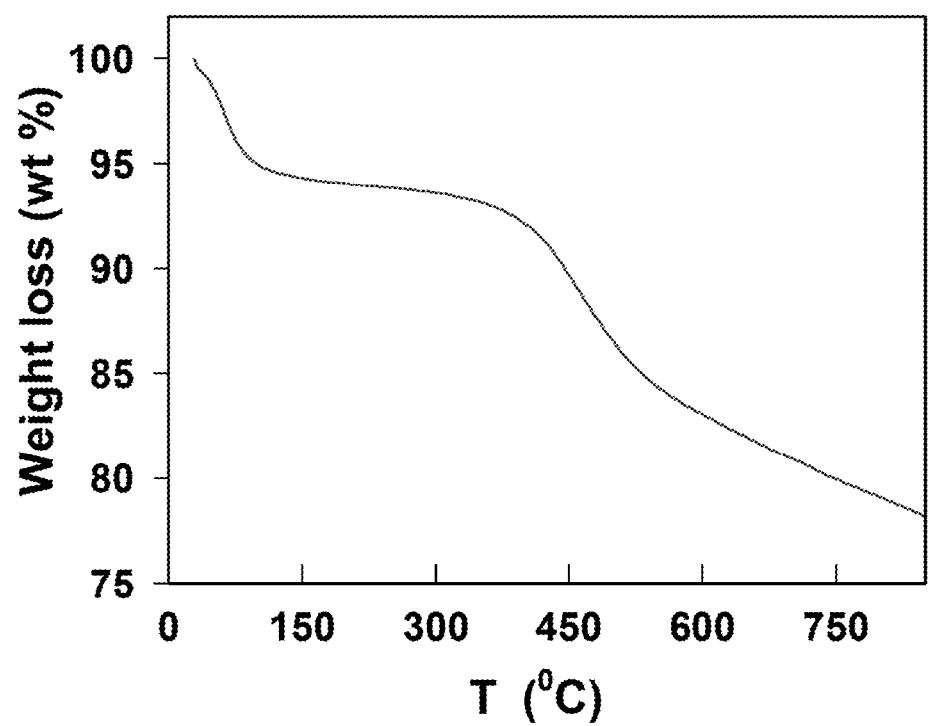
FIG. 4 represents a thermogravimetric thermogram of a nanostructured material, which is obtained from the pyrolysis of date palm leaflets at 850° C.

In addition, the TGA curve (FIG. 4) showed two sharp weight loss zones, one from 30 to 103° C. and the other from 380 to 600° C. About 5.1% of the initial weight of the sample was lost during the heating up to 100° C., which may have resulted from the loss of water molecules. The sharp weight loss between 380 and 600° C. may have been due to the decomposition of oxygen containing fraction of $NSCE_{850}$. The obtained weight at 600° C. was 17% of that of the original sample. Upon increasing the temperature further, the weight of the sample decreased slowly. The obtained weight at 850° C. was 73% of the original $NSCE_{850}$.

EXAMPLE 4

FESEM and EDS Analysis of NSCE

The $NSCE_{1500}$ was planner type as the original sample of DPL. FIGS. 7A, 7B, and 7C show the FE-SEM images of $NSCE_{1500}$. $NSCE_{1500}$ was observed, in FIGS. 7A and 7B, to consist of an interconnected nanostructured sheet with high surface roughness. The high-magnification image (FIG. 7C) of $NSCE_{1500}$ clearly showed the presence of nanospheres and nanohemispheres as well as the interconnected nanosheet. The pyrolysis of the DPL at 850° C. also generated a planar (nearly two-dimensional) type of structure as observed in a photograph (NSCE in FIG. 1) and in FIGS. 9A and 9B. The initially brown DPL sample turned into a black sample upon heating at 850° C. (NSCE in FIG. 1). The FESEM images (FIGS. 8A and 8B) of this as-prepared carbon showed the presence of interconnected nanostructured sheets with high surface roughness, similar to that of $NSCE_{1500}$. The high-magnification image (FIG. 8C) of $NSCE_{850}$ more clearly showed the presence of nanospheres and nanohemispheres as well as the interconnected nanosheet, similar to that of $NSCE_{1500}$.

The EDS analysis of $NSCE_{850}$ confirmed the presence of C, O, N, Fe, Si, K, and Ca (data not shown). Generally, carbon prepared at around 850° C. from lingo-cellulose-type materials contains some oxygen as well as carbon. The other EDS-detected elements in $NSCE_{850}$, i.e., N, Fe, Si, K and Ca, are also found in the date palm [Trabzuni D M, Ahmed S E B, Abu-Tarboush H M, (2014) Chemical Composition Minerals and Antioxidants of the Heart of Date Palm from Three Saudi Cultivars, Food and Nutrition Sciences, 5: 1379-1386].

To confirm the planar (nearly two-dimensional) type structure of the $NSCE_{850}$, we recorded FESEM images (FIG. 9A (side-view) and FIG. 9B (top view)) at low magnifications of the $NSCE_{850}$. The obtained thickness of the $NSCE_{850}$ is 214.67 μM which is very small with compared to the corresponding length and width. This analysis concludes that the $NSCE_{850}$ has nearly a planar structure.

EXAMPLE 5

Raman Analysis of NSCE

Figure 10:
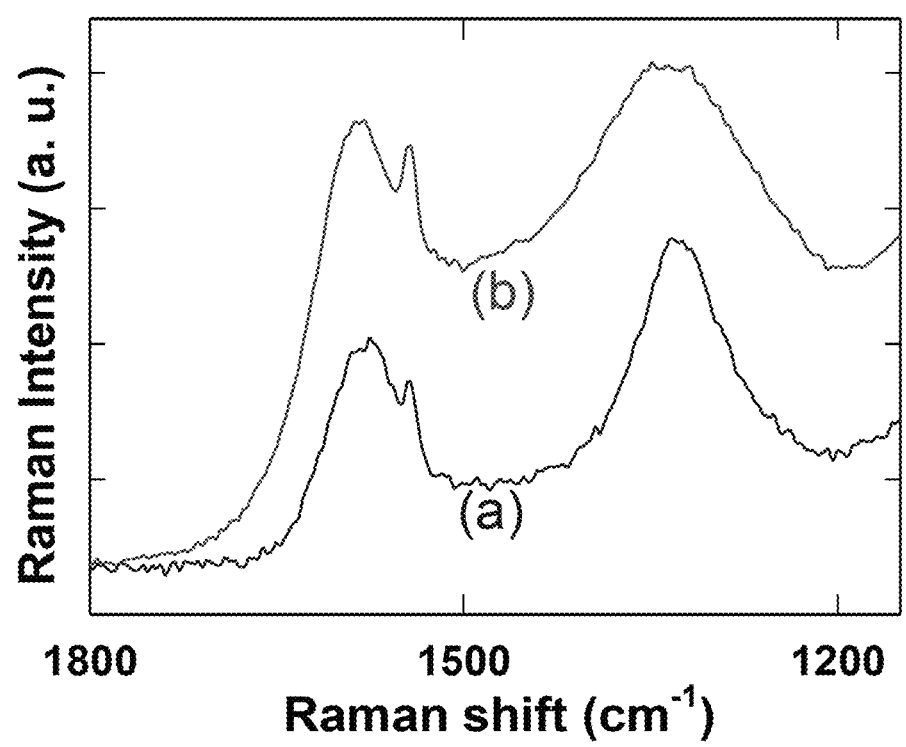
FIG. 10 represents a Raman spectrum of the nanostructured material, which is obtained from the pyrolysis of date palm leaflets at (a) 1,500° C.; and (b) 850° C.

FIGS. 10(a) and 10(b) show the Raman spectra of $NSCE_{1500}$ and $NSCE_{850}$, respectively. $NSCE_{1500}$ yielded distinct Raman peaks at 1333.4 $cm^{-1}$ (D band), and 1575.74 $cm^{-1}$ (G band), which were related to graphitic ($sp^2$) carbon peaks [Amiinu I S, Zhang J, Kou Z, Liu X, Asare O K, Zhou H, Cheng K, Zhang H, Mai L, Pan M, Mu S, (2016) Self-Organized 3D Porous Graphene Dual-Doped with Biomass-Sponsored Nitrogen and Sulfur for Oxygen Reduction and Evolution, ACS Appl. Mater. Interfaces, 8: 29408-29418; Kudin K N, Ozbas B, Schniepp H C, Prud'homme R K, Aksay I A, Car R, (2008) Raman spectra of graphite oxide and functionalized graphene sheets, Nano Letters, 8: 36-41]. D and G bands of $NSCE_{850}$ appeared at 1338.34 $cm^{-1}$ and 1580.14 $cm^{-1}$, respectively. Both $NSCE_{1500}$ and $NSCE_{850}$ also showed one other sharp peak, at 1544 $cm^{-1}$, which was related to amorphous carbon. However, the intensity of this 1544 $cm^{-1}$ peak of $NSCE_{850}$ was greater than that of $NSCE_{1500}$, suggesting that $NSCE_{1500}$ contained lower amounts of amorphous carbon than that of $NSCE_{850}$. Also, the D and G bands of $NSCE_{850}$ were observed to be much broader than those of $NSCE_{1500}$. Higher disorder in graphite has been generally observed to lead to broader G and D bands [Kudin K N, Ozbas B, Schniepp H C, Prud'homme R K, Aksay I A, Car R, (2008) Raman spectra of graphite oxide and functionalized graphene sheets, Nano Letters, 8: 36-41]. The pyrolysis of DPL at 1500° C. thus appeared to have formed more ordered graphitic carbon than did the pyrolysis at 850° C., consistent with the TGA-DSC analysis.

The above results also indicated that carbon obtained by heating DPLs to 1500° C. is a good candidate to be used as a working electrode. However, due to the higher manufacturing cost, only the $NSCE_{850}$ was used for further characterization.

EXAMPLE 6

XPS Analysis of NSCE

Figure 11A:
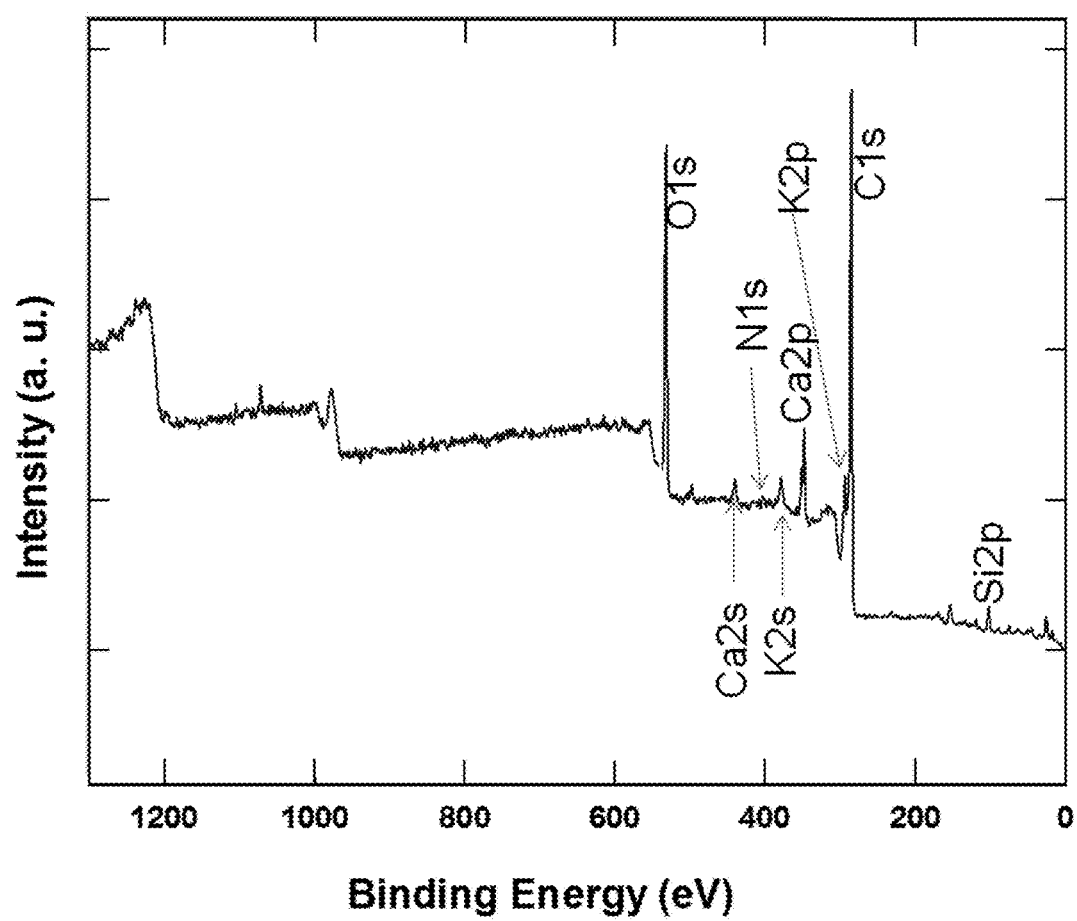
FIG. 11A represents an XPS spectrum of the nanostructured material, which is obtained from the pyrolysis of date palm leaflets at 850° C.
Figure 11B:
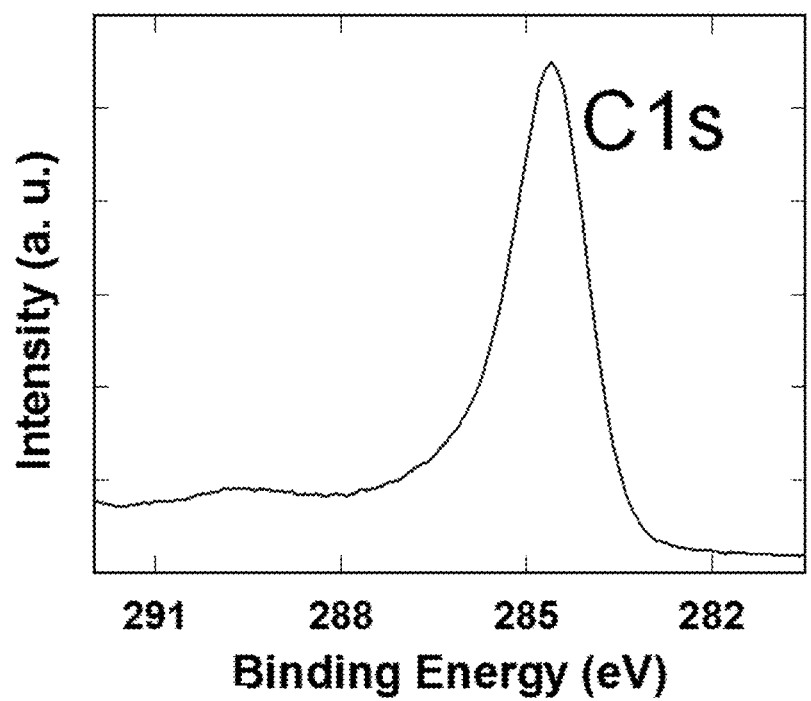
FIG. 11B represents a zoomed-in XPS spectrum of the nanostructured material, which is obtained from the pyrolysis of date palm leaflets at 850° C.
Figure 11C:
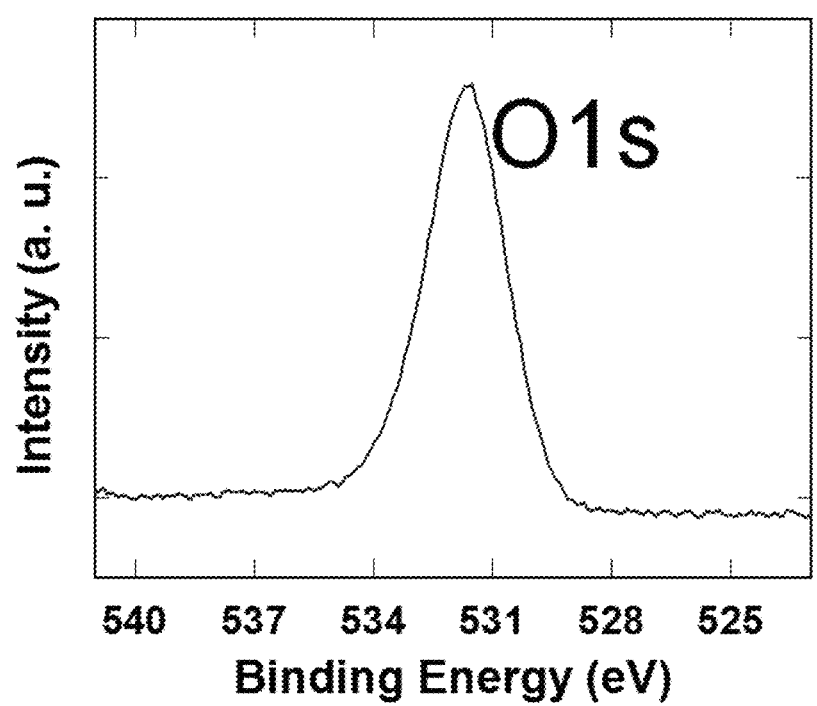
FIG. 11C represents another zoomed-in XPS spectrum of the nanostructured material, which is obtained from the pyrolysis of date palm leaflets at 850° C.

FIGS. 11A, 11B, and 11C show the XPS spectra of $NSCE_{850}$. The survey XPS spectrum confirmed the presence of C, O, N, Si, K, and Ca in $NSC_{850}$. The same elements were also identified by EDS analyses as discussed in "FESEM and EDS analyses of NSCE section". The EDS analysis identified Fe also in $NSCE_{850}$. However, we did not detect the presence of a peak for Fe in the XPS spectrum. The reason of the absence of the Fe in XPS might be the deeply buried it in the $NSCE_{850}$ as our current XPS setup can detect only the element on surface. The major XPS peaks of $NSCE_{850}$ were appeared for C and O which indicated the major components of $NSCE_{850}$ were C and O. The high resolution scan for C1s indicated the presence of graphitic C, C—O, —C=O and —C—OOH [Huang Y, Peng L, Liu Y, Zhao G, Chen J Y, Yu G, (2016) Bio-based Nano Porous Active Carbon Fibers for High-Performance Supercapacitors, ACS Appl. Mater. Interfaces, 8: 15205-15215]. Besides, the high resolution scan for O1s indicated the presence of C—O—H, —C—O—C— and —COOR in $NSC_{850}$ [Huang Y, Peng L, Liu Y, Zhao G, Chen J Y, Yu G, (2016) Bio-based Nano Porous Active Carbon Fibers for High-Performance Supercapacitors, ACS Appl. Mater. Interfaces, 8: 15205-15215].

EXAMPLE 7

BET Analysis of NSCE

Figure 5:
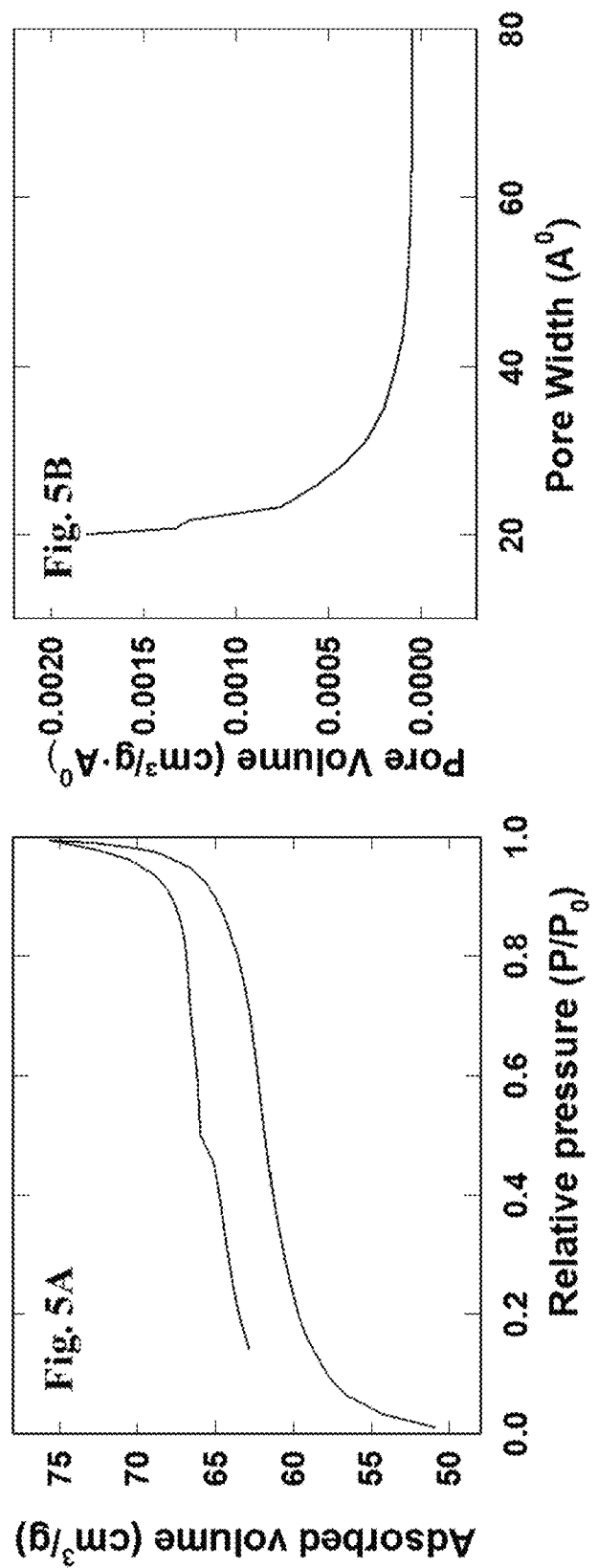
FIG. 5A represents adsorption-desorption isotherms of the nanostructured material, which is obtained from the pyrolysis of date palm leaflets at 850° C.
FIG. 5B represents pore distribution of the nanostructured material, which is obtained from the pyrolysis of date palm leaflets at 850° C.

Surface attributes, such as surface area, pore size, and pore volume of prepared samples were studied by BET surface area analysis. FIG. 5A shows the classical type-II pattern of nitrogen adsorption desorption isotherm that reflects the mesoporosity of the sample. Gradient in adsorption curve clearly indicated the presence of external surface area in the sample. The BET surface area was measured to be around 201.5 $m^2 \cdot g^{-1}$. The pore diameter of sample was measured to be 2.1 nm (FIG. 5B).

EXAMPLE 8

Electrochemical Properties of NSCE with Respect to $K_4[Fe(CN)_6]$

FIGS. 12A(a) and 12A(b) show the cyclic voltammograms (CVs) of NSCEss, respectively, in the absence and the presence of 5 mM $K_4[Fe(CN)_6]$ in 0.1 M KCl (five cycles). In the absence of $K_4[Fe(CN)_6]$, $NSCE_{850}$ generated relatively stable and flat current curves (i.e., without any peaks) in both the forward and backward scans; that is, it generated a stable background current throughout the applied potential window. In the presence of $K_4[Fe(CN)_6]$, $NSCE_{850}$ generated a well-defined anodic peak at 0.272 V, which was due to the oxidation of $Fe^{2+}$ to $Fe^{3+}$. In the subsequent reverse scan, one cathodic peak appeared at 0.165 V (yielding a $\Delta E_p$ of 107 mV), which was due to the reduction of $Fe^{3+}$ (generated during the anodic scan) to $Fe^{2+}$. Both peak currents changed just a little from the first cycle to the second cycle during the recording of the CVs in the presence of $K_4[Fe(CN)_6]$ at $NSCE_{850}$, and the peak currents and CV shapes of subsequent cycles were nearly identical to those of the second cycle. The relatively small change in the peak current from the first cycle to the second may have been due the stabilization of the electrode. This type of phenomenon has been observed for other nano/micro-structured modified electrodes [A. N. Kawde, M. A. Aziz, (2014) Porous copper-modified graphite pencil electrode for the amperometric detection of 4-nitrophenol, Electroanalysis, 26: 2484-2490]. We compared the electrocatalytic properties of $NSCE_{850}$ and the GCE by also recording CVs using the GCE. Five consecutive CV cycles of the GCE both in the absence and presence of 5 mM $K_4[Fe(CN)_6]$ in 0.1 M KCl were recorded as shown in FIGS. 12B(a) and 12B(b), respectively. The GCE showed a lower background current than did our prepared $NSCE_{850}$. The increased background of our prepared $NSCE_{850}$ likely resulted from the interconnected nanostructured carbon (and hence higher surface area), whereas the GCE showed flat bulk carbon surfaces (and hence a relatively low surface area). The background current of bulk GCEs has been previously shown to increase upon immobilization of nanostructured carbon materials such as carbon nanotubes [N. S. Lawrence, R. P. Deo, J. Wang, (2004) Electrochemical determination of hydrogen sulfide at carbon nanotube modified electrodes, Analytica Chimica Acta, 517: 131-137]. In the presence of $K_4[Fe(CN)_6]$, the GCE generated one anodic peak at 0.373 V and one cathodic peak at 0.087 V, yielding a $\Delta E_p$ of 286 mV. This $\Delta E_p$ value was 179 mV greater than that obtained with our prepared $NSCE_{850}$. In addition, the redox current of $K_4[Fe(CN)_6]$ at the GCE was much lower than that obtained at the $NSCE_{850}$ electrode. Also, the peak current of $K_4[Fe(CN)_6]$ at the GCE did perceptibly change from cycle to cycle in our tests. The above results indicated the electrochemical properties of $NSCE_{850}$, in particular its electrocatalytic properties and stability, to be superior to those of the commonly employed standard GCE.

Figure 13:
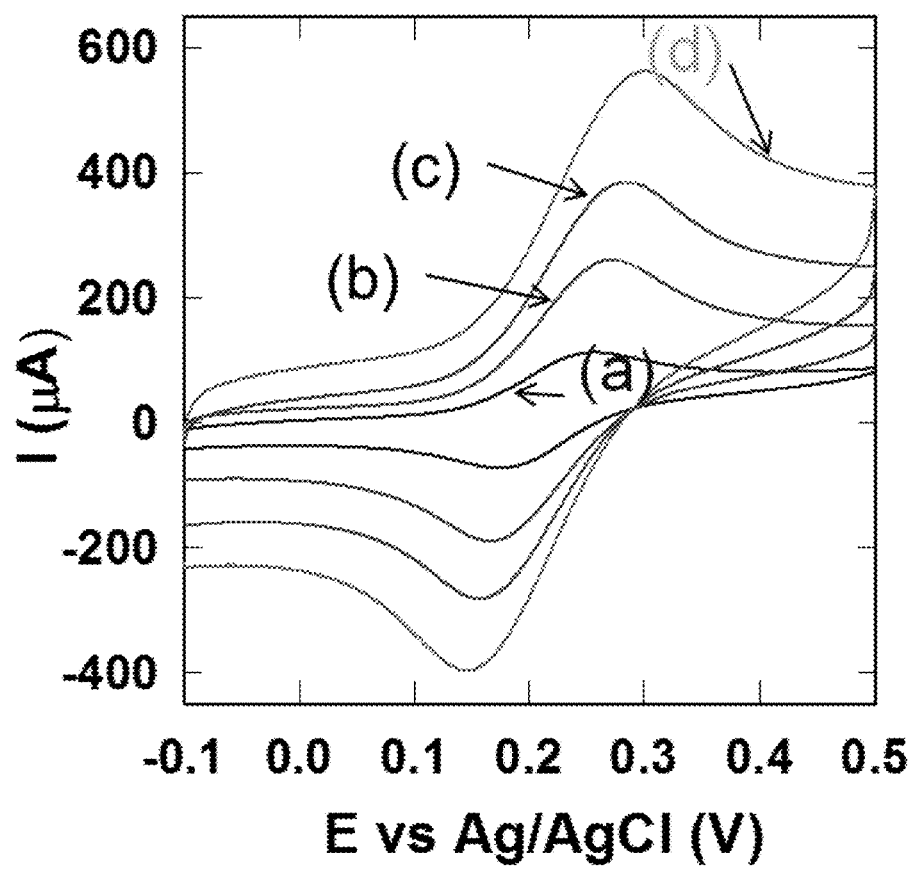
FIG. 13 represents cyclic voltammograms of an electrochemical cell having a working electrode comprising the nanostructured material, which is obtained from the pyrolysis of date palm leaflets at 850° C., an electrolyte comprising 0.1 M KCl and 5.0 mM $K_4[Fe(CN)_6]$, and (a) at a scan rate of 10 millivolts per second; (b) at a scan rate of 50 millivolts per second; (c) at a scan rate of 100 millivolts per second; and (d) at a scan rate of 200 millivolts per second.
Figure 14:
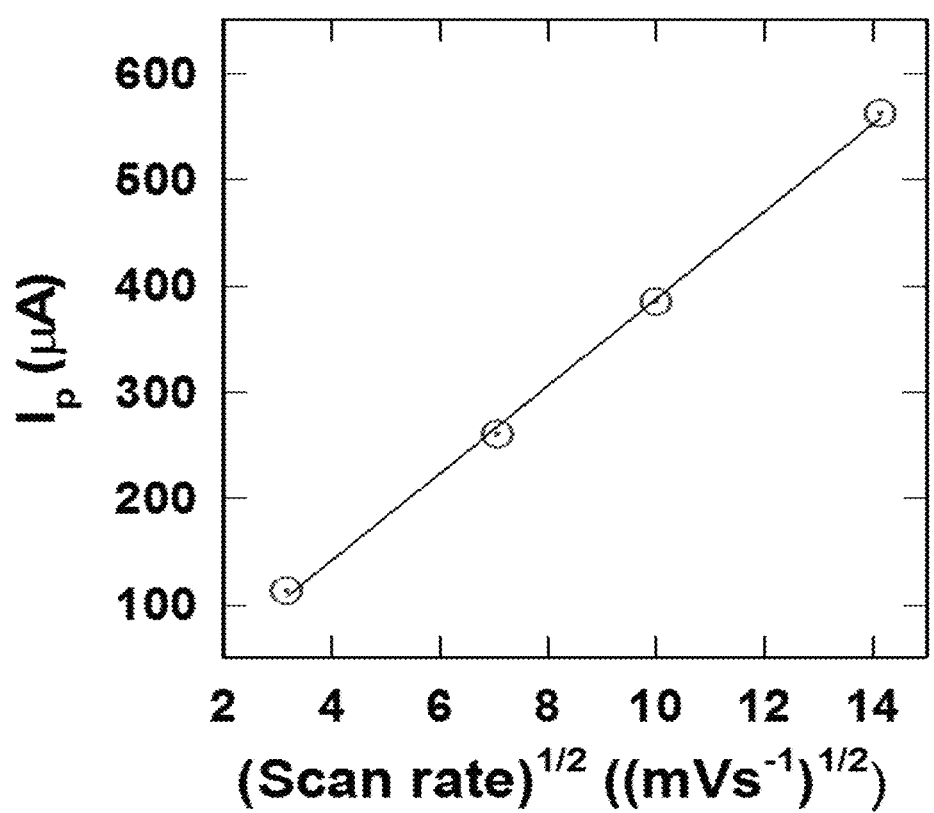
FIG. 14 represents a correlation curve between anodic peak current and cyclic voltammetry scan rates.

Separately, the scan rate dependence of the CVs was measured for $NSCE_{850}$ in an electrolyte solution containing 0.1 M KCl and 5 mM $K_4[Fe(CN)_6]$ (FIG. 13). The peak current and $\Delta E_p$ values increased as the scan rate was increased from 10 mV/s to 200 mV/s. FIG. 14 shows the corresponding plot of the anodic peak current as a function of the square root of the scan rate (Randles-Sevcik plot). The plot was linear over the full range of scan rates tested ($R^2$=0.996), indicating that the reaction process was diffusion controlled [Bakare F O, Mahfoz W, Aziz M A, Shaikh M N, Hakeem A S, Oyama M, Yamani Z H, (2016) Preparation and electrochemical properties of a gallium-doped zinc oxide electrode decorated with densely gathered palladium nanoparticles, Journal of The Electrochemical Society, 163: H24-H29].

EXAMPLE 9

Electrochemical Properties of NSCE with Respect to Hydroquinone

Figure 6:
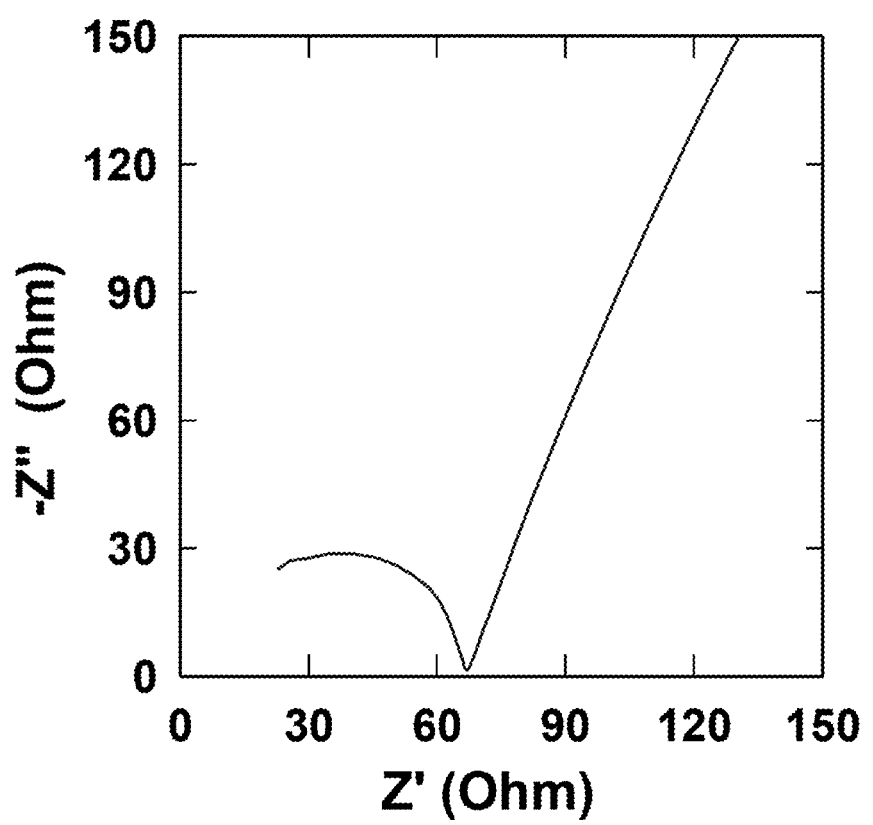
FIG. 6 represents an electrochemical impedance spectrum of the nanostructured material, which is obtained from the pyrolysis of date palm leaflets at 850° C., when exposed to a solution containing 0.1 M KCl, 2.5 mM $K_3Fe(CN)_6$, and 2.5 mM $K_4Fe(CN)_6$, under a voltage of 0.22 volts in a frequency range of 0.1 to $10^6$ Hz.
Figure 15:
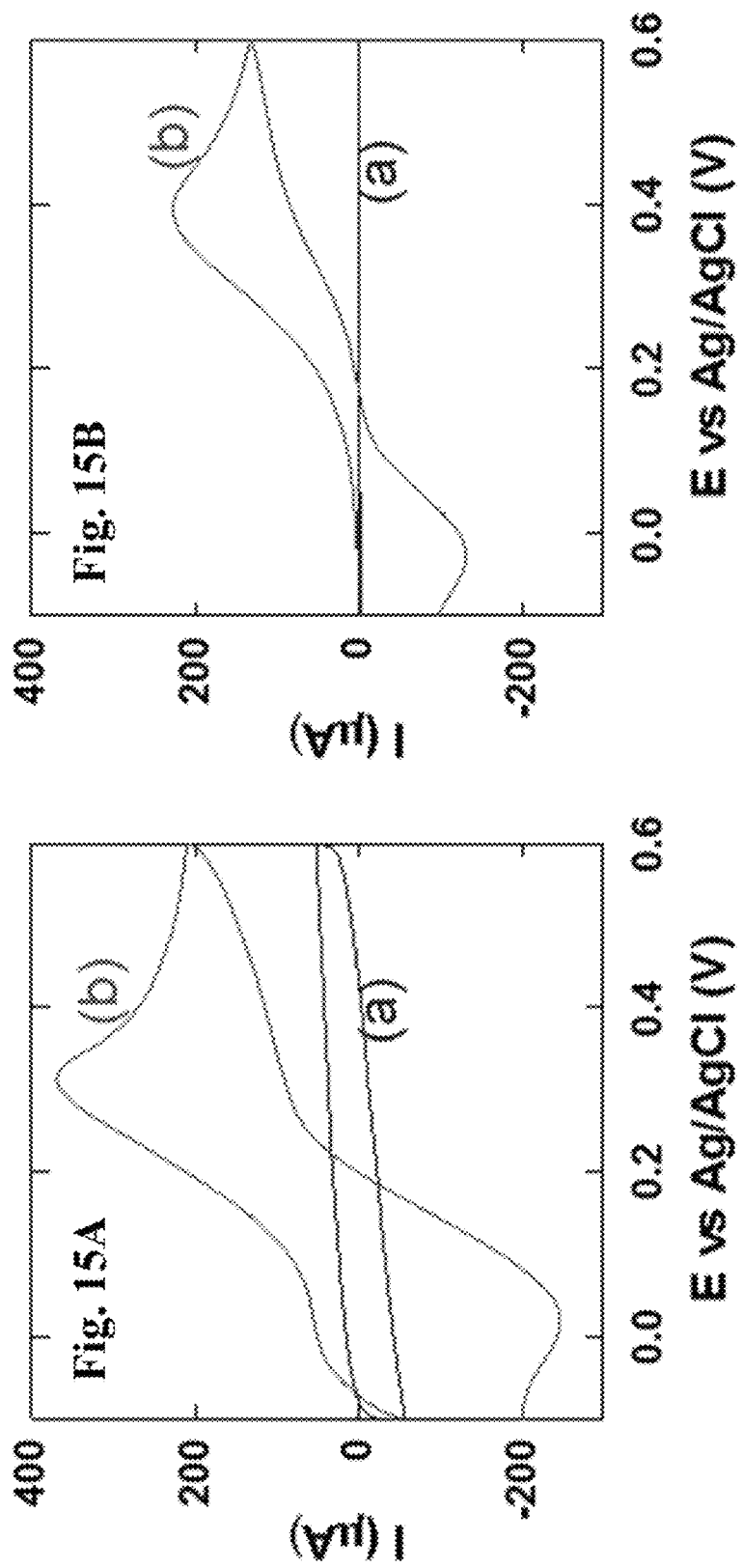
FIG. 15A represents cyclic voltammograms of an electrochemical cell having a working electrode comprising the nanostructured material, which is obtained from the pyrolysis of date palm leaflets at 850° C. and (a) an electrolyte comprising 0.1 M acetate buffer; and (b) an electrolyte comprising 0.1 M acetate buffer and 5.0 mM hydroquinone.
FIG. 15B represents cyclic voltammograms of an electrochemical cell having a glassy carbon electrode and (a) an electrolyte comprising 0.1 M acetate buffer; and (b) an electrolyte comprising 0.1 M acetate buffer and 5.0 mM hydroquinone.

In our next trial, we investigated the electrocatalytic properties of $NSCE_{850}$ and the GCE toward the electrochemical reaction of HQ. FIGS. 15A(a) and 15A(b) show the CVs of $NSCE_{850}$ in, respectively, the absence and the presence of 5 mM HQ in 0.1 M acetate buffer (pH 7). Comparing these two CVs clearly showed that $NSCE_{850}$ had very high electrocatalytic properties toward HQ. The oxidation and successive reduction peaks appeared at 0.315 and 0.015 V, yielding a $\Delta E_p$ of 0.300 V. To compare the electrocatalytic properties of $NSCE_{850}$ with those of the GCE, we also recorded the CVs of the GCE in the absence and the presence of 5 mM HQ in 0.1 M acetate buffer (pH 7) (FIGS. 15B(a) and 15B(b)). The oxidation and successive reduction peaks of HQ appeared at 0.400 and −0.028 V, yielding a $\Delta E_p$ of 0.428, which was 128 mV higher than the $\Delta E_p$ of $NSCE_{850}$. Moreover, the electrochemical redox current and oxidation potential of HQ at $NSCE_{850}$ was higher and lower, respectively, than that obtained at the bare GCE, i.e., our developed $NSCE_{850}$ showed better electrocatalytic properties toward HQ than did the widely used GCE. In addition, an electrochemical impedance of $NSCE_{850}$ was measured (as shown in FIG. 6) The impedance studied suggest that electron transfer between the $NSCE_{850}$ and redox probe ($Fe^{2+}/Fe^{3+}$) is very first.

EXAMPLE 10

Electrochemical Impedance Analysis of NSCE

In order to clarify the electrochemical performance of the electrode, electrochemical impedance spectroscopy (EIS) was also employed as a technique for the electrochemical characterization of $NSCE_{850}$. FIG. 6 shows the impedance spectra represented as Nyquist plots for carbon leaf electrode in 0.1 M KCl containing 2.5 mM $K_3Fe(CN)_6$ and 2.5 mM $K_4Fe(CN)_6$ and in the frequency range of $0.1$-$10^6$ Hz. In the Electrochemical impedance spectroscopy, the semicircle part corresponds to electron transfer limited process and its diameter is equal to the electron transfer resistance, $R_{ct}$ that controls electron transfer kinetics of redox probe at the electrode interface. The low electron transfer resistance (FIG. 6) suggests the easy electron transfer between the $NSCE_{850}$ and redox probe ($Fe^{2+}/Fe^{3+}$).

EXAMPLE 11

Amperometric Determination of Hydroquinone Concentration

Figure 16:
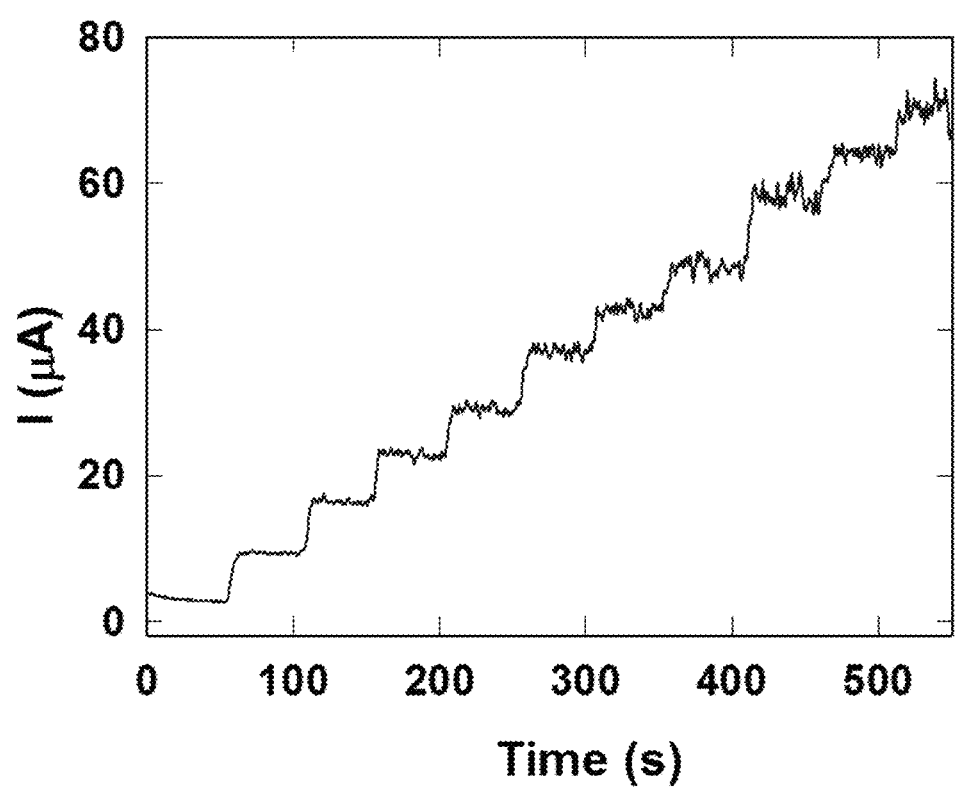
FIG. 16 represents an amperogram of an electrochemical cell having a working electrode comprising the nanostructured material, which is obtained from the pyrolysis of date palm leaflets at 850° C., and an electrolyte comprising 0.1 M acetate buffer, wherein a voltage of +0.3 volts is applied to the working electrode (relative to a reference electrode of the electrochemical cell), and wherein 50 μM of hydroquinone is successively added to the electrolyte at a constant time interval.

The dependence of the current on HQ concentration and the limit of detection of HQ for $NSCE_{850}$ were measured by using the amperometry method. FIG. 16 shows a typical amperogram of $NSCE_{850}$ at an applied potential of 0.3 V upon successive addition of 50 μM HQ. A well-defined and sensitive signal resulted from every addition of HQ. The relationship between the response current (after subtracting the mean of the zero HQ response) and the HQ concentration was found to be linear over the HQ concentration range 50-500 μM (FIG. 17) and to follow the linear regression equation concentration-dependent signal=0.1366 [HQ]−0.4207 ($R^2$=0.9995). The limit of detection of the $NSCE_{850}$ sensor for HQ, based on three standard deviations of the obtained signal in the absence of HQ, was calculated to be around 6.1 μM.

Figure 18:
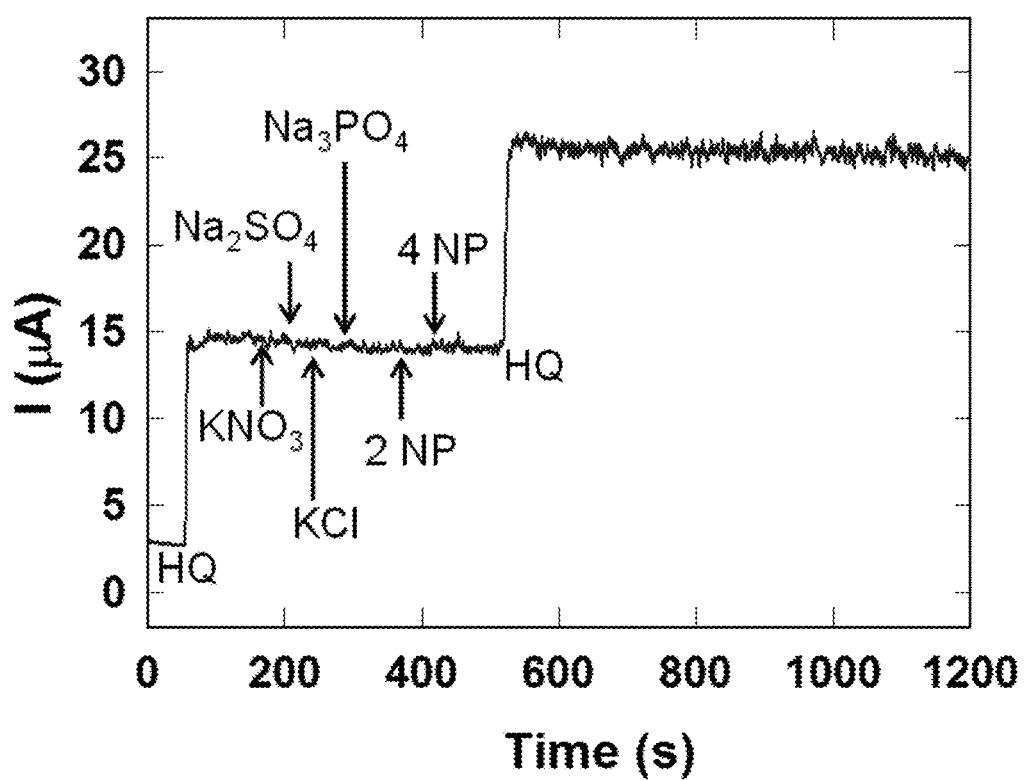
FIG. 18 represents an amperogram of an electrochemical cell having a working electrode comprising the nanostructured material, which is obtained from the pyrolysis of date palm leaflets at 850° C., and an electrolyte comprising 0.1 M acetate buffer, wherein a voltage of +0.3 volts is applied to the working electrode (relative to a reference electrode of the electrochemical cell), and wherein hydroquinone, $Na_2SO_4$, KCl, $Na_3PO_4$, 2-nitrophenol, 4-nitrophenol, and hydroquinone are successively added to the electrolyte.

FIG. 18 shows amperograms of $NSCE_{850}$ at an applied potential of 0.3 V upon successive addition of HQ, $KNO_3$, $Na_2SO_4$, $Na_3PO_4$, 2NP, 4NP, and again HQ. After addition of 100 μM HQ, a well-defined signal was observed. Further successive addition of 100 μM of each of $KNO_3$, $Na_2SO_4$, 0.1 M $Na_3PO_4$, 2NP and 4 NP did not change the intensity of the initial HQ signal. This result indicated our sensor to be highly selective for HQ and to completely avoid the effects from the other interferent species. Upon addition of another aliquot of 100 μM HQ, a well-defined signal was generated again and this signal was stable for a long period of time. This result indicated the high stability of the fabricated $NSCE_{850}$ electrode.

Substrate-free carbon electrodes, each consisting of interconnected nanostructured carbon, were prepared by carrying out pyrolysis of date palm leaflets and were used for electrochemical applications. The elemental compositions of these electrodes were identified by EDS and XPS analysis. The electrocatalytic properties of these electrodes were evaluated by recording the corresponding CVs in the absence and the presence of $K_4[Fe(CN)_6]$ and HQ in solutions of 0.1 M supporting electrolyte. The voltammetry studies revealed the electrocatalytic properties of these electrodes to be superior to those of the GCE. The prepared nanostructured carbon electrodes showed a low detection limit for HQ with high analytical selectivity, sensitivity, and stability due to the electrocatalytic activities.

The invention claimed is:
1. An electrode, comprising:
    a nanostructured material comprising pyrolyzed date palm leaves,
    wherein the nanostructured material has a thickness in the range of 10 to 1,000 μm, and
    wherein the pyrolyzed date palm leaves are obtained from a pyrolysis of an agro-waste comprising date palm leaves in an inert gas and in a temperature range of 800 to 1600° C.
2. The electrode of claim 1, wherein the inert gas is selected from the group consisting of nitrogen, helium, neon, and argon.
3. The electrode of claim 1, wherein the agro-waste consists of date palm leaves.
4. The electrode of claim 1, wherein the nanostructured material is not disposed on a substrate.
5. The electrode of claim 1, further comprising:
    a conductive material,
    wherein the nanostructured material is disposed on the conductive material with an adhesive.
6. The electrode of claim 1, wherein the nanostructured material further comprises at least one element selected from the group consisting of oxygen, nitrogen, iron, silicon, potassium, and calcium.
7. The electrode of claim 1, wherein the nanostructured material is porous with an average pore size of 1 to 10 nm.
8. An electrode comprising:
    a nanostructured material comprising pyrolvzed date palm leaves,
    wherein the pyrolyzed date palm leaves are obtained from a pyrolysis of an agro-waste comprising date palm leaves in an inert gas and in a temperature range of 800 to 1600° C. and
    wherein the nanostructured material comprises carbon walls that are arranged in a stacked configuration.
9. An electrochemical cell, comprising:
    a working electrode comprising
        a nanostructured material comprising pyrolyzed date palm leaves, wherein the nanostructured material has a thickness in the range of 10 to 1,000 μm and wherein the pyrolyzed date palm leaves are obtained from a pyrolysis of an agro-waste comprising date palm leaves in an inert gas and in a temperature range of 800 to 1600° C.;
    a reference electrode; and
    a counter electrode,
    wherein the reference electrode and the counter electrode are in ionic communication with the working electrode via an electrolyte.

10. The electrochemical cell of claim 9, wherein the electrolyte comprises hydroquinone.

11. The electrochemical cell of claim 9, wherein the reference electrode comprises silver-silver chloride.

12. The electrochemical cell of claim 9, wherein the counter electrode comprises platinum.

13. A method of determining a hydroquinone concentration in a hydroquinone-containing solution with the electrochemical cell of claim 9, comprising:
   contacting the hydroquinone-containing solution with the working electrode, the counter electrode, and the reference electrode of the electrochemical cell;
   applying a voltage to the working electrode relative to the reference electrode to oxidize at least a portion of hydroquinone in the hydroquinone-containing solution thereby generating an electric current in the electrochemical cell; and
   determining the hydroquinone concentration in the hydroquinone-containing solution based on the electric current.

14. The method of claim 13, wherein a detection limit of the electrochemical cell is in the range of 1.0 to 10.0 μM of hydroquinone.

15. The method of claim 13, wherein the hydroquinone concentration in the hydroquinone-containing solution is in the range of 1.0 μM to 1.0 M.

16. The method of claim 13, wherein the hydroquinone concentration is determined at a temperature in the range of 10 to 40° C.

17. The method of claim 13,
   wherein the hydroquinone-containing solution comprises hydroquinone and at least one of a halide, a sulfate, a nitrate, a phosphate, an acetate of an alkali metal, and nitrophenol, and
   wherein a hydroquinone selectivity of the electrochemical cell is at least 95% by mole.

18. The method of claim 13, wherein the voltage is in the range of 0.05 to 0.5 volts relative to the reference electrode.

19. The method of claim 13, wherein the hydroquinone concentration is determined from a calibration curve that linearly relates the electric current to the hydroquinone concentration.

* * * * *